United States Patent
Oida et al.

(10) Patent No.: US 12,262,974 B2
(45) Date of Patent: Apr. 1, 2025

(54) BRAIN MEASUREMENT APPARATUS AND BRAIN MEASUREMENT METHOD

(71) Applicants: HAMAMATSU PHOTONICS K.K., Hamamatsu (JP); Kyoto University, Kyoto (JP)

(72) Inventors: Takenori Oida, Hamamatsu (JP); Takahiro Moriya, Hamamatsu (JP); Akinori Saito, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 149 days.

(21) Appl. No.: 17/829,428

(22) Filed: Jun. 1, 2022

(65) Prior Publication Data

US 2022/0386873 A1    Dec. 8, 2022

(30) Foreign Application Priority Data

Jun. 4, 2021   (JP) ................. 2021-094331

(51) Int. Cl.
*A61B 5/00*     (2006.01)
*A61B 5/055*    (2006.01)
(Continued)

(52) U.S. Cl.
CPC ............ *A61B 5/0042* (2013.01); *A61B 5/055* (2013.01); *A61B 5/245* (2021.01); *A61B 5/6803* (2013.01);
(Continued)

(58) Field of Classification Search
None
See application file for complete search history.

(56) References Cited

U.S. PATENT DOCUMENTS

| | | |
|---|---|---|
| 8,305,078 B2 | 11/2012 | Savukov et al. |
| 8,519,705 B2 | 8/2013 | Savukov et al. |

(Continued)

FOREIGN PATENT DOCUMENTS

| | | |
|---|---|---|
| CN | 110728704 A | 1/2020 |
| JP | H11-505356 A | 5/1999 |

(Continued)

OTHER PUBLICATIONS

Boto et al. ("Moving magnetoencephalography towards real-world applications with a wearable system", Nature, V. 255, 2018 (Year: 2018).*

(Continued)

*Primary Examiner* — Patrick Fernandes
*Assistant Examiner* — Marjan Saboktakin
(74) *Attorney, Agent, or Firm* — Faegre Drinker Biddle & Reath LLP

(57) ABSTRACT

A brain measurement apparatus configured to generate an MR image and a brain's magnetic field distribution of a subject includes: an MRI module having a transmission coil configured to transmit a transmission pulse toward the subject and a detection coil configured to detect a nuclear magnetic resonance signal generated in the subject by the transmission pulse; an optically pumped magnetometer configured to detect a brain's magnetic field of the subject; a generator configured to generate the MR image based on the nuclear magnetic resonance signal detected by the detection coil and generating the brain's magnetic field distribution based on the brain's magnetic field detected by the optically pumped magnetometer; a marker displayed on the MR image generated by the generator; and a helmet-type frame to which the detection coil, the optically pumped magnetometer, and the marker are attached and which is attached to a head of the subject.

7 Claims, 8 Drawing Sheets

(51) Int. Cl.
  *A61B 5/245* (2021.01)
  *G01R 33/00* (2006.01)
  *G01R 33/022* (2006.01)
  *G01R 33/032* (2006.01)
  *G01R 33/26* (2006.01)
  *G01R 33/385* (2006.01)

(52) U.S. Cl.
  CPC ..... *G01R 33/0076* (2013.01); *G01R 33/0094* (2013.01); *G01R 33/022* (2013.01); *G01R 33/032* (2013.01); *G01R 33/26* (2013.01); *G01R 33/385* (2013.01); *A61B 2562/0223* (2013.01)

(56) References Cited

U.S. PATENT DOCUMENTS

| | | | |
|---|---|---|---|
| 2009/0112084 A1* | 4/2009 | Piferi | A61N 1/0529 600/421 |
| 2015/0219732 A1 | 8/2015 | Diamond et al. | |
| 2021/0121066 A1 | 4/2021 | Rheineck et al. | |
| 2021/0386347 A1 | 12/2021 | Moriya et al. | |

FOREIGN PATENT DOCUMENTS

| | | |
|---|---|---|
| JP | 2013-523201 A | 6/2013 |
| JP | 5823195 B2 | 11/2015 |
| JP | 2020-146408 A | 9/2020 |
| WO | WO-97/006744 A1 | 2/1997 |
| WO | 2011/117471 A1 | 9/2011 |

OTHER PUBLICATIONS

Boto, Elena et al., "Moving magnetoencephalography towards real-world applications with a wearable system," Nature, Mar. 29, 2018, vol. 555, pp. 657-661.

Iivanainen, Joonas et al., "On-scalp MEG system utilizing an actively shielded array of optically-pumped magnetometers," NeuroImage, 2019, 194, pp. 244-258.

Körber, Rainer et al., "SQUIDs in biomagnetism: a roadmap towards improved healthcare," Supercond. Sci. Technol. 113001 (30pp), 2016 vol. 29, pp. 1-30.

Tsai, L. L. et al., "An Open-Access, Very-Low-Field MRI System for Posture-Dependent $^3$He Human Lung Imaging," J Magn Reson., Aug. 2008, 193(2), pp. 1-29.

Uchida Akira, et al., "Integrated Visualization System for MEG and MRI Data", Medical and Imaging Technology, vol. 20, No. 5, Sep. 30, 2002, p. 593-p. 598.

* cited by examiner

BRAIN MEASUREMENT APPARATUS AND BRAIN MEASUREMENT METHOD

TECHNICAL FIELD

The present disclosure relates to a brain measurement apparatus and a brain measurement method.

BACKGROUND

Patent Literature 1 (Japanese Patent No. 5823195) describes an MEG (magnetoencephalography) apparatus using an optically pumped magnetometer. In the MEG apparatus, the distribution of a minute magnetic field on the sensor surface is measured by an optically pumped magnetometer. Here, since the magnetic field distribution and an MR image, which is an image obtained by imaging the structure of the subject's brain using an MRI (magnetic resonance imaging) apparatus, are aligned (registered) with each other, it is possible to acquire the position and direction of an equivalent current dipole moment vector when a magnetic field generation source generated by the neural activity in the subject's brain is assumed as the equivalent current dipole moment vector. In addition, in Non-Patent Literature 1 ("SQUIDs in biomagnetism: a roadmap towards improved healthcare", Supercond. Sci. Technol. 29 (2016) 113001 (30 pp)) describes a study of integrating the MEG apparatus and the MRI apparatus.

In general, the MEG apparatus and the MRI apparatus are separate apparatuses. Therefore, in order to acquire the magnetic field distribution (brain's magnetic field distribution) associated with the neural activity in the subject's brain, a separate measurement for aligning the brain's magnetic field distribution due to the magnetic field measured on the sensor surface with the MR image of the subject's brain is required in addition to the measurement in both the apparatuses. However, in the alignment by the measurement, the measurement performed separately and the integrated processing of the brain's magnetic field distribution and the magnetoencephalographic MR image based on the measurement become a new factor of the error. In addition, Non-Patent Literature 1 describes that it is necessary to improve the accuracy of the alignment even when the MEG apparatus and the MRI apparatus are integrated.

SUMMARY

Therefore, it is an object of the present disclosure to provide a brain measurement apparatus and a brain measurement method capable of aligning a brain's magnetic field distribution with an MR image more accurately.

A brain measurement apparatus according to the present disclosure is a brain measurement apparatus configured to generate an MR image and a brain's magnetic field distribution of a subject, and includes: an MRI module having a transmission coil configured to transmit a transmission pulse toward the subject and a detection coil configured to detect a nuclear magnetic resonance signal generated in the subject by the transmission pulse; an optically pumped magnetometer configured to detect a brain's magnetic field of the subject; a generator configured to generate the MR image based on the nuclear magnetic resonance signal detected by the detection coil and to generate the brain's magnetic field distribution based on the brain's magnetic field detected by the optically pumped magnetometer; a marker displayed on the MR image generated by the generator; and a helmet-type frame to which the detection coil, the optically pumped magnetometer, and the marker are attached and which is attached to a head of the subject.

Alternatively, a brain measurement method according to the present disclosure is a brain measurement method for generating an MR image and a brain's magnetic field distribution of a subject, and includes: a first step in which, in a state in which a helmet-type frame provided with an optically pumped magnetometer and a marker is attached to a head of the subject, a nuclear magnetic resonance signal generated in the subject and the marker is detected to generate the MR image including the marker, based on the nuclear magnetic resonance signal, and a brain's magnetic field of the subject is detected by an optically pumped magnetometer to generate the brain's magnetic field distribution based on the brain's magnetic field; and a second step in which the MR image and the brain's magnetic field distribution generated in the first step are aligned with each other.

In the brain measurement apparatus and the brain measurement method, since the marker and the optically pumped magnetometer are attached to the frame, the positional relationship between the marker and the optically pumped magnetometer is determined by the machining accuracy in the frame. This means that the position of the marker can be acquired with high accuracy according to the machining accuracy in the brain's magnetic field distribution generated based on the brain's magnetic field detected by the optically pumped magnetometer. On the other hand, the marker is displayed on the MR image. Therefore, it is possible to acquire information regarding the positional relationship between the brain's magnetic field distribution and the MR image based on the position of the marker in the brain's magnetic field distribution and the position of the marker in the MR image. Therefore, it is possible to align the brain's magnetic field distribution with the MR image more accurately. In addition, since the head position of the subject with respect to the gradient magnetic field coil may change during the measurement of MRI and MEG, it is not easy to align the MR image with the brain's magnetic field distribution. On the other hand, in the brain measurement apparatus and the brain measurement method, since the marker provided on the helmet-type frame to which the optically pumped magnetometer is fixed is used, the position of the marker is displayed on the MR image. Therefore, it is possible to align the brain's magnetic field distribution with the MR image more accurately.

In the brain measurement apparatus according to the present disclosure, the generator may perform: an extraction process the marker from the MR image; an acquisition process acquiring a position of the marker extracted by the extraction process in an MRI coordinate system that is a coordinate system on the MR image; an estimation process estimating conversion information configured to convert a magnetoencephalographic coordinate system, which is a coordinate system on the brain's magnetic field distribution, into the MRI coordinate system based on a position of the marker in the magnetoencephalographic coordinate system and the position of the marker in the MRI coordinate system acquired by the acquisition process; and an alignment process performing alignment between the brain's magnetic field distribution and the MR image by projecting the brain's magnetic field distribution onto the MRI coordinate system using the conversion information estimated by the estimation process. In addition, in the brain measurement method according to the present disclosure, the second step may include: an extraction step extracting the marker from the MR image; an acquisition step acquiring a position of the marker extracted in the extraction step in an MRI coordinate system that is a coordinate system on the MR image; an estimation step estimating conversion information configured to convert a magnetoencephalographic coordinate system, which is a coordinate system on the brain's magnetic field distribution, into the MRI coordinate system based on a position of the marker in the magnetoencephalographic coordinate system and the position of the marker in the MRI coordinate system acquired in the acquisition step; and an alignment step performing alignment between the brain's magnetic field distribution and the MR image by projecting the brain's magnetic field distribution onto the MRI coordinate system using the conversion information estimated in the estimation step. In these cases, since the conversion information configured to convert the magnetoencephalographic coordinate system into the MRI coordinate system is estimated from the position of the marker in the MR image and the brain's magnetic field distribution and the brain's magnetic field distribution is projected onto the MRI coordinate system based on the conversion information, it is possible to accurately align the MR image with the brain's magnetic field distribution.

The brain measurement apparatus according to the present disclosure may further include multiple markers attached to different positions of the frame. In this case, since there are multiple reference points in the alignment between the brain's magnetic field distribution and the MR image, it is possible to align the brain's magnetic field distribution with the MR image more accurately, for example, as compared with a case where there is only one marker.

In the brain measurement apparatus according to the present disclosure, the multiple markers may include at least three markers that are not on the same straight line. In this case, since the three reference points required for the alignment between the brain's magnetic field distribution and the MR image are acquired more accurately, it is possible to align the brain's magnetic field distribution with the MR image more accurately, for example, as compared with a case where there are two markers.

In the brain measurement apparatus according to the present disclosure, the marker may include a Beekley marker or a Magnevist solution capsule. In this case, since the marker is displayed more clearly as a bright spot in the MR image, the position of the marker is specified more accurately. Therefore, it is possible to align the brain's magnetic field distribution with the MR image more accurately.

According to the present disclosure, it is possible to provide a brain measurement apparatus and a brain measurement method capable of aligning the brain's magnetic field distribution and the MR image more accurately.

DETAILED DESCRIPTION

Figure 1:
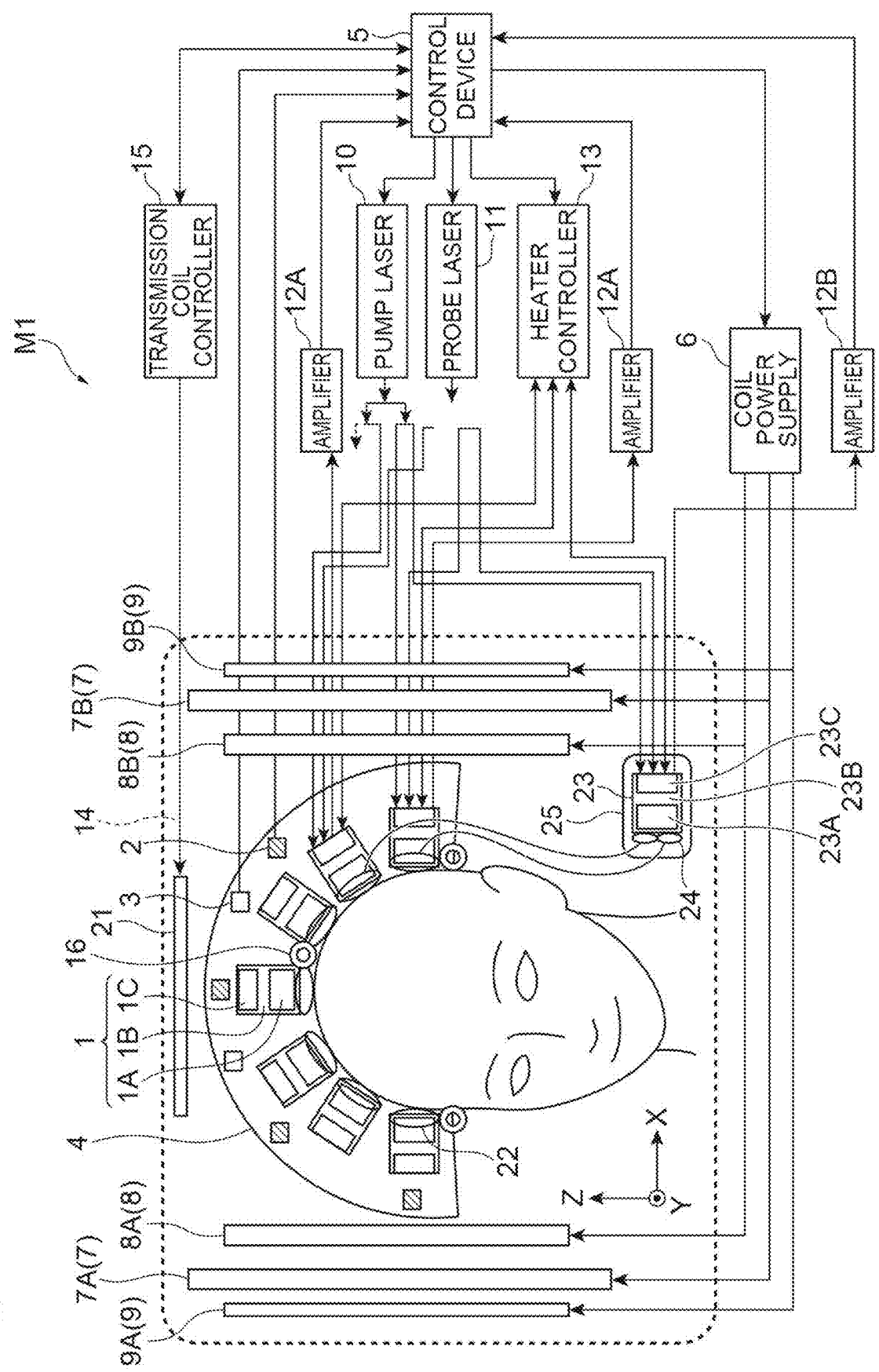
FIG. 1 is a diagram showing the configuration of a brain measurement apparatus according to an embodiment.

Hereinafter, an embodiment will be described in detail with reference to the diagrams. In addition, in the description of the diagrams, the same or repeated elements are denoted by the same reference numerals, and repeated description thereof may be omitted. In addition, the following diagrams may show a Cartesian coordinate system defined by the X axis, the Y axis, and the Z axis.

FIG. 1 is a schematic diagram showing the configuration of a brain measurement apparatus M1 according to an embodiment. The brain measurement apparatus M1 is an apparatus for measuring a brain's magnetic field and a magnetic resonance (MR) image for a subject. That is, the brain measurement apparatus M1 is an apparatus for generating a brain's magnetic field distribution and an MR image of a subject. The brain measurement apparatus M1 includes: a magnetoencephalograph module having multiple optically pumped magnetometer (OPM) modules 1, multiple magnetic sensors for geomagnetic field cancellation 2, multiple magnetic sensors for active shield 3, a non-magnetic frame 4 (frame), a pair of geomagnetic field nulling coils 7, a pair of gradient magnetic field nulling coils 8 (geomagnetic field nulling coils), and a pair of active shield coils 9; and an MRI module having a transmission coil 21, a receive coil 22 (detection coil), an OPM module 23, and an output coil 24. In addition, the brain measurement apparatus M1 includes a control device (generator) 5, a coil power supply 6, a pump laser 10, a probe laser 11, amplifiers 12A and 12B, a heater controller 13, an electromagnetic shield 14, a transmission coil controller 15, a marker 16, and a magnetic shield 25.

In the following description, a direction approximately parallel to the central axis of the head of the subject is defined as a Z-axis direction and directions perpendicular to the Z axis and perpendicular to each other are defined as an X-axis direction and a Y-axis direction.

Each OPM module 1 includes an optically pumped magnetometer 1A, a heat insulating material 1B, and a read circuit 1C. The multiple OPM modules 1 are arranged at predetermined intervals along the scalp, for example.

The optically pumped magnetometer 1A is a sensor that measures a brain's magnetic field by using optical pumping. That is, the optically pumped magnetometer 1A is a sensor for detecting the brain's magnetic field of the subject. The optically pumped magnetometer 1A has a sensitivity of, for example, about 10 fT to 10 pT. The heat insulating material 1B prevents heat transfer of the optically pumped magnetometer 1A. The read circuit 1C is a circuit for acquiring the detection result of the optically pumped magnetometer 1A. The optically pumped magnetometer 1A emits pump light to a cell containing alkali metal vapor to excite the alkali metal.

The excited alkali metal is in a spin polarization state, and when this receives magnetic field, the inclination of the spin polarization axis of the alkali metal atom changes according to the magnetic field. The inclination of the spin polarization axis is detected by probe light emitted separately from the pump light. In addition, the optically pumped magnetometer 1A is configured such that a predetermined bias magnetic field is applied in the emission direction of the pump light so as to be sensitive to a magnetic field having a frequency included in the range of 0 to 200 Hz. The read circuit 1C receives probe light passing through the alkali metal vapor by a photodiode and acquires the detection result. The read circuit 1C outputs the detection result to the amplifier 12A.

The optically pumped magnetometer 1A may be, for example, an axial gradiometer. The axial gradiometer has a measurement region and a reference region in a direction perpendicular to the scalp (measurement location) of the subject and coaxially. The measurement region is, for example, a location closest to the scalp of the subject among locations where the axial gradiometer measures the brain's magnetic field. The reference region is, for example, a location away from the measurement region by a predetermined distance (for example, 3 cm) in a direction away from the scalp of the subject, among locations where the axial gradiometer measures the brain's magnetic field. The axial gradiometer outputs the respective measurement results in the measurement region and the reference region to the amplifier 12A. Here, when common mode noise is included, its influence is shown in each of the output result of the measurement region and the output result of the reference region. Common mode noise is removed by acquiring the difference between the output result of the measurement region and the output result of the reference region. By removing the common mode noise, the optically pumped magnetometer 1A can obtain a sensitivity of about 10 $fT/\sqrt{Hz}$, for example, when performing measurement in a magnetic noise environment of 1 pT.

The magnetic sensor for geomagnetic field cancellation 2 is a sensor that measures a magnetic field relevant to the geomagnetic field at a position corresponding to the optically pumped magnetometer 1A, and is, for example, a flux gate sensor having a sensitivity of about 1 nT to 100 µT. The position corresponding to the optically pumped magnetometer 1A is a position around (near) the region where the optically pumped magnetometer 1A is arranged. The magnetic sensor for geomagnetic field cancellation 2 may be provided so as to correspond to the optically pumped magnetometer 1A in a one-to-one manner, or may be provided so as to correspond in a one-to-many manner (one magnetic sensor for geomagnetic field cancellation 2 for multiple optically pumped magnetometers 1A). The magnetic sensor for geomagnetic field cancellation 2 measures, for example, geomagnetic field and a gradient magnetic field of the geomagnetic field (hereinafter, simply referred to as "gradient magnetic field") as magnetic fields relevant to the geomagnetic field, and outputs the measured value to the control device 5. The measured value of the magnetic sensor for geomagnetic field cancellation 2 can be expressed by a vector having a direction and a magnitude. The magnetic sensor for geomagnetic field cancellation 2 may continuously perform measurement and output at predetermined time intervals.

The magnetic sensor for active shield 3 is a sensor that measures a fluctuating magnetic field at a position corresponding to the optically pumped magnetometer 1A, and is, for example, an optically pumped magnetometer having a sensitivity of about 100 fT to 10 nT and different from the optically pumped magnetometer 1A. The position corresponding to the optically pumped magnetometer 1A is a position around (near) the region where the optically pumped magnetometer 1A is arranged. The magnetic sensor for active shield 3 may be provided so as to correspond to the optically pumped magnetometer 1A in a one-to-one manner, or may be provided so as to correspond in a one-to-many manner (one magnetic sensor for active shield 3 for the multiple optically pumped magnetometers 1A). The magnetic sensor for active shield 3 measures a magnetic field of a noise (AC) component of, for example, 200 Hz or less as a fluctuating magnetic field, and outputs the measured value to the control device 5. The measured value of the magnetic sensor for active shield 3 can be expressed by a vector having a direction and a magnitude. The magnetic sensor for active shield 3 may continuously perform measurement and output at predetermined time intervals.

The marker 16 is a marker displayed on the MR image acquired by the control device 5, and includes, for example, a Beekley marker or a Magnevist solution capsule. The marker 16 has, for example, a spherical shape. The marker 16 including the Beekley marker or the Magnevist solution capsule is displayed as a bright spot in the MR image because the marker 16 has a sufficient proton density and appropriate longitudinal relaxation time T1 and lateral relaxation time T2.

The non-magnetic frame 4 is a frame that covers the entire scalp of the subject whose brain's magnetic field is to be measured, and is formed of a non-magnetic material such as graphite whose relative magnetic permeability is close to 1 and accordingly does not affect the magnetic field distribution. The non-magnetic frame 4 can be, for example, a helmet-type frame that surrounds the entire scalp of the subject and is attached to the head of the subject. The multiple optically pumped magnetometers 1A are fixed to the non-magnetic frame 4 so as to be close to the scalp of the subject. In addition, the magnetic sensor for geomagnetic field cancellation 2 is fixed to the non-magnetic frame 4 so that a magnetic field relevant to the geomagnetic field at the position of each of the multiple optically pumped magnetometers 1A can be measured, and the magnetic sensor for active shield 3 is fixed to the non-magnetic frame 4 so that a fluctuating magnetic field at the position of each of the multiple optically pumped magnetometers 1A can be measured. Since a change in the magnetic field strength according to the position of the fluctuating magnetic field is smaller than that in the case of the static magnetic field, a smaller number of magnetic sensors for active shield 3 than the number of magnetic sensors for geomagnetic field cancellation 2 may be fixed to the non-magnetic frame 4.

In addition, one or more markers 16 attached to different positions are attached to the non-magnetic frame 4. Here, multiple markers 16 are used. In the example shown in FIGS. 1 and 2A, the multiple markers 16 include at least three markers 16 that are not on the same straight line in the non-magnetic frame 4. In addition, the receive coil 22 for detecting a nuclear magnetic resonance signal for MR image measurement is fixed to the scalp side of the subject of the multiple optically pumped magnetometers 1A inside the non-magnetic frame 4. The receive coil 22 is a coil for detecting a nuclear magnetic resonance signal generated in the subject. The receive coil 22 detects the nuclear magnetic resonance signal of the proton, which will be described later, and converts the nuclear magnetic resonance signal into an electric current. In order to improve the detection sensitivity of the nuclear magnetic resonance signal, it is preferable that the receive coil 22 is provided on the side of the optically pumped magnetometer 1A close to the scalp of the head of the subject. As described above, at least the receive coil 22, the optically pumped magnetometer 1A, and the marker 16 are attached to the non-magnetic frame 4.

Figure 2A:
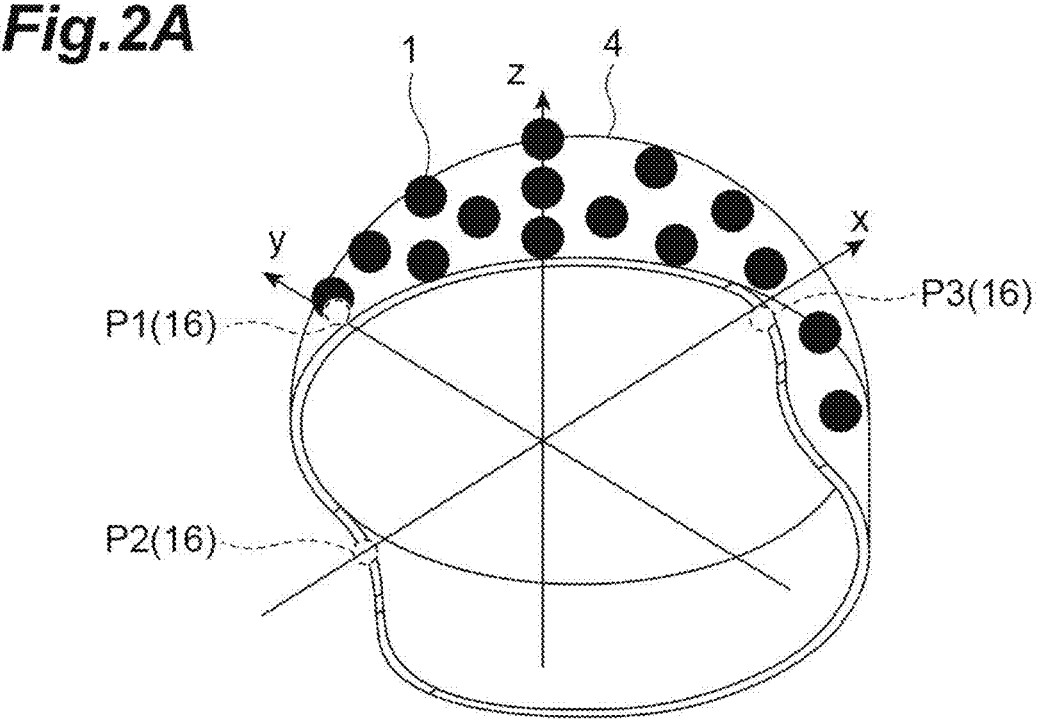
FIG. 2A is a schematic diagram showing an example of a non-magnetic frame according to the embodiment.

FIG. 2A is a diagram showing an example of the non-magnetic frame 4. In the example shown in FIG. 2A, the non-magnetic frame 4 that is a helmet type frame is shown, and multiple OPM modules 1 and markers P1, P2, and P3, which are three markers 16, are attached to the non-magnetic frame 4. The non-magnetic frame 4 is attached to the subject. The multiple OPM modules 1 are attached, for example, along the outer surface of the frame at predetermined intervals. The marker P1 is attached to a position corresponding to the glabella of the subject, and the markers P2 and P3 are attached to positions corresponding to the left and right temples of the subject's head.

FIG. 1 is referred to again. The transmission coil 21 is a coil for emitting an RF pulse (transmission pulse) having a predetermined frequency (for example, about 300 kHz) to the head of the subject during MR image measurement. That is, the transmission coil 21 is a coil for transmitting a transmission pulse toward the subject. Then, a nuclear magnetic resonance signal is generated from the subject by the transmission pulse. The transmission coil 21 is arranged above the head of the subject outside the non-magnetic frame 4, for example.

The output coil 24 is electrically connected to both ends of the receive coil 22 through a cable, and receives a current flowing through both ends of the receive coil 22, converts the current into a magnetic signal again, and outputs the magnetic signal.

Similar to the OPM module 1, the OPM module 23 includes an optically pumped magnetometer 23A (another optically pumped magnetometer), a heat insulating material 23B, and a read circuit 23C. The OPM module 23 is housed in, for example, a magnetic shield 25 that shields a static magnetic field, which will be described later, outside the non-magnetic frame 4 together with the output coil 24. The magnetic shield 25 is formed of, for example, mu-metal having a relative magnetic permeability of more than 1.

The optically pumped magnetometer 23A is a sensor that measures a magnetic signal using optical pumping. In addition, the optically pumped magnetometer 23A is configured such that a predetermined bias magnetic field is applied in the emission direction of pump light so as to be sensitive to a magnetic field having a frequency included in the range of 20 kHz to 500 kHz. For example, a bias magnetic field of about 40 µT is applied so as to be sensitive to the frequency of 300 kHz of the electromagnetic wave emitted by the proton. The optically pumped magnetometer 23A detects a magnetic signal output by the output coil 24. The read circuit 23C outputs the detection result of the optically pumped magnetometer 23A to the amplifier 12B.

Figure 3:
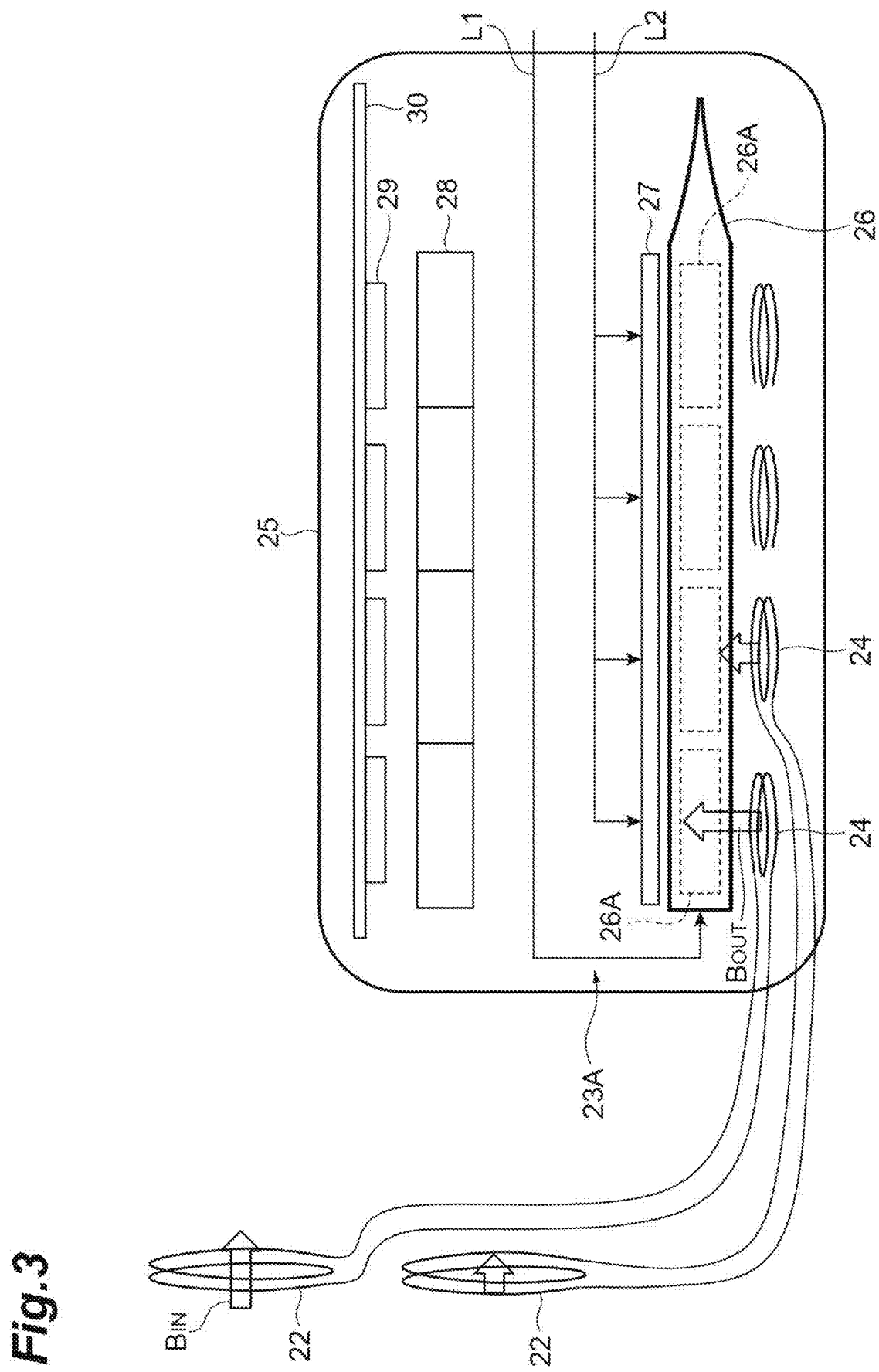
FIG. 3 is a schematic diagram showing the configuration of an OPT module according to the embodiment.

FIG. 3 shows a specific example of the configuration of the OPM module 23. The optically pumped magnetometer 23A includes a longitudinal cell 26 filled with a gas containing an alkali metal whose direction of polarization changes with a magnetic field to be measured, a heater 27 that heats the entire cell 26 to a predetermined temperature (for example, 180°), a polarization beam splitter 28, and a photodetector 29. Pump light L1 is introduced into the cell 26 from the outside along the longitudinal direction of the inside of the cell 26. In addition, along a direction perpendicular to the longitudinal direction, probe light L2 from the outside is branched and emitted to multiple crossing regions 26A (for example, four crossing regions 26A) divided in the longitudinal direction. The polarization angle of the probe light L2 transmitted through the crossing regions 26A is detected by the polarization beam splitter 28 and the photodetector 29 provided corresponding to each of the crossing regions 26A. That is, the polarization beam splitter 28 separates the probe light L2 into two linearly polarized components perpendicular to each other, and the photodetector 29 detects the intensities of the two linearly polarized components using two built-in photodiodes (PDs) and detects the polarization angle of the probe light L2 based on the ratio of the detected intensities. A circuit board 30 is further provided in the OPM module 23. Through the read circuit 23C in the circuit board 30, the polarization angle of the probe light L2 detected for each crossing region 26A is output.

In the magnetic shield 25, the output coil 24 is fixed so as to face each crossing region 26A of the cell 26 in the OPM module 23 having the above-described configuration. With such a configuration, a magnetic signal $B_{OUT}$ generated by the output coil 24 based on the electromagnetic field $E_{OUT}$ detected by the receive coil 22 is detected based on the polarization angle of the probe light L2 that changes according to the inclination of the spin polarization axis of the alkali metal atom. Here, in the example of FIG. 3, the number of divided crossing regions 26A is four, but may be changed to any number. In addition, multiple cells 26 may be provided in parallel, so that the crossing regions 26A are arrayed in a two-dimensional manner (for example, 4×4=16).

When measuring the brain's magnetic field, the control device 5 determines currents for various coils based on the measured values output from the magnetic sensor for geomagnetic field cancellation 2 and the magnetic sensor for active shield 3, and outputs a control signal for outputting each of the currents to the coil power supply 6. Based on the measured values of the multiple magnetic sensors for geomagnetic field cancellation 2, the control device 5 determines a current for the geomagnetic field nulling coil 7 and the gradient magnetic field nulling coil 8, which are geomagnetic field nulling coils, so as to generate a magnetic field for canceling a magnetic field relevant to the geomagnetic field. In addition, based on the measured values of the multiple magnetic sensors for active shield 3, the control device 5 determines a current for the active shield coil 9 so as to generate a magnetic field for canceling a fluctuating magnetic field. The control device 5 outputs a control signal corresponding to the determined current to the coil power supply 6.

Specifically, the control device 5 determines a current for the geomagnetic field nulling coil 7 so that the average value of the measured values of the multiple magnetic sensors for geomagnetic field cancellation 2 approaches zero (as a result, a magnetic field opposite to the geomagnetic field at the position of the optically pumped magnetometer 1A and having approximately the same magnitude as the geomagnetic field is generated). The control device 5 outputs a control signal (control signal for static magnetic field cancellation) corresponding to the determined current of the geomagnetic field nulling coil 7 to the coil power supply 6.

In addition, the control device 5 determines a current for the gradient magnetic field nulling coil 8 so that the deviation from the average value of the measured values of the multiple magnetic sensors for geomagnetic field cancellation 2 is minimized (as a result, a magnetic field opposite to the gradient magnetic field at the position of the optically pumped magnetometer 1A and having approximately the same magnitude as the gradient magnetic field is generated). The control device 5 outputs a control signal (control signal for static magnetic field cancellation) corresponding to the determined current of the gradient magnetic field nulling coil 8 to the coil power supply 6.

In addition, the control device 5 determines a current for the active shield coil 9 so that the average value of the measured values of the multiple magnetic sensors for active shield 3 approaches zero (as a result, a magnetic field opposite to the fluctuating magnetic field at the position of the optically pumped magnetometer 1A and having approximately the same magnitude as the fluctuating magnetic field is generated). The control device 5 outputs a control signal (control signal for fluctuating magnetic field cancellation) corresponding to the determined current of the active shield coil 9 to the coil power supply 6.

In addition, the control device 5 obtains information regarding the magnetic field detected by the optically pumped magnetometer 1A by using the signal output from the amplifier 12A. Then, the control device 5 generates the brain's magnetic field distribution based on the brain's magnetic field detected by the optically pumped magnetometer 1A (based on information regarding the magnetic field). When the optically pumped magnetometer 1A is an axial gradiometer, the control device 5 may remove the common mode noise by acquiring the difference between the output result of the measurement region and the output result of the reference region. In addition, the control device 5 may control operations such as the emission timing and the emission time of the pump laser 10 and the probe laser 11. In addition, the process of generating the brain's magnetic field distribution from the information regarding the magnetic field detected by the optically pumped magnetometer 1A can be performed by using the known technique.

In addition, when measuring the MR image, the control device 5 determines a current to be supplied to each of the geomagnetic field nulling coil 7 and the gradient magnetic field nulling coil 8, which operate as coils for applying the static magnetic field and the gradient magnetic field, respectively, and outputs a control signal for outputting the current to the coil power supply 6. That is, the control device 5 determines a current flowing through the geomagnetic field nulling coil 7 so that an X-axis direction magnetic field having a predetermined strength (for example, 7 mT) is applied to the head of the subject as a static magnetic field. In addition, the control device 5 selectively determines an X-axis direction magnetic field gradient ($dB_x/dX$), a Y-axis direction magnetic field gradient ($dB_x/dY$), and a Z-axis direction magnetic field gradient ($dB_x/dZ$) as a gradient magnetic field to determine a current flowing through the gradient magnetic field nulling coil 8. Therefore, a slicing position in the MR image can be determined, and the position within the slice surface can be encoded by phase encoding and frequency encoding. In addition, when measuring the MR image, the control device 5 outputs a control signal so that no current is supplied to the active shield coil 9 for removing low-frequency noise.

In addition, when measuring the MR image, the control device 5 outputs a control signal, which is for controlling electric power supplied to the transmission coil 21, to the transmission coil controller 15, so that control to emit a transmission pulse having a predetermined frequency (for example, about 300 kHz when the strength of the static magnetic field is 7 mT) to the head of the subject is performed. As a result, protons on the slice surface (surface selected by the static magnetic field and the gradient magnetic field) resonate to tilt the spin. Thereafter, the control device 5 controls the electric power of the transmission coil 21 to be turned off. As a result, it is possible to acquire the MR image by measuring how the spin returns based on the output of the OPM module 23. That is, the control device 5 generates an MR image based on the magnetic signal detected by the optically pumped magnetometer 23A. In other words, the control device 5 is also a generator that generates an MR image based on the nuclear magnetic resonance signal detected by the receive coil 22 (output of the receive coil 22). More specifically, the control device 5 measures the nuclear magnetic resonance signal from the proton by encoding the position with frequency and phase using a known spin echo sequence or gradient echo sequence, and converts the measurement result into an MR image using FFT.

The control device 5 is physically configured to include a memory such as a RAM and a ROM, a processor (arithmetic circuit) such as a CPU, a communication interface, and a storage unit such as a hard disk. Examples of the control device 5 include a personal computer, a cloud server, a smartphone, and a tablet terminal. The control device 5 functions by executing a program stored in the memory on the CPU of the computer system.

The coil power supply 6 outputs a predetermined current to each of the geomagnetic field nulling coil 7, the gradient magnetic field nulling coil 8, and the active shield coil 9 in response to the control signal output from the control device 5. Specifically, the coil power supply 6 outputs a current to the geomagnetic field nulling coil 7 in response to the control signal relevant to the geomagnetic field nulling coil 7. The coil power supply 6 outputs a current to the gradient magnetic field nulling coil 8 in response to the control signal relevant to the gradient magnetic field nulling coil 8. The coil power supply 6 outputs a current to the active shield coil 9 in response to the control signal relevant to the active shield coil 9.

The transmission coil controller 15 is electrically connected to the transmission coil 21, and supplies electric power to the transmission coil 21 in response to the control signal output from the control device 5 so that a transmission pulse having a predetermined frequency is emitted.

The geomagnetic field nulling coil 7 is a coil for cancelling the magnetic field of the geomagnetic field among the magnetic fields relevant to the geomagnetic field at the position of the optically pumped magnetometer 1A. The geomagnetic field nulling coil 7 generates a magnetic field according to the current supplied from the coil power supply 6 to cancel the geomagnetic field. The geomagnetic field nulling coil 7 has, for example, a pair of geomagnetic field nulling coils 7A and 7B. The pair of geomagnetic field nulling coils 7A and 7B are arranged with the optically pumped magnetometer 1A interposed therebetween (for example, on the left and right of the subject). The pair of geomagnetic field nulling coils 7A and 7B generate a magnetic field, which is opposite to the geomagnetic field at the position of the optically pumped magnetometer 1A and has approximately the same magnitude as the geomagnetic field, according to the current supplied from the coil power supply 6. The direction of the magnetic field is, for example, the X-axis direction, the Y-axis direction, and the Z-axis direction. The geomagnetic field at the position of the optically pumped magnetometer 1A is canceled by a magnetic field generated by the geomagnetic field nulling coil 7, the magnetic field being opposite to the geomagnetic field and having approximately the same magnitude as the geomagnetic field. In this manner, the geomagnetic field nulling coil 7 cancels the geomagnetic field at the position of the optically pumped magnetometer 1A.

In addition, the geomagnetic field nulling coil 7 has a role as a static magnetic field coil for generating a static magnetic field in the X-axis direction during MR image measurement. The geomagnetic field nulling coil 7 generates a static magnetic field having a predetermined strength according to the current supplied from the coil power supply 6.

The gradient magnetic field nulling coil 8 is a coil for cancelling the gradient magnetic field among the magnetic fields relevant to the geomagnetic field at the position of the optically pumped magnetometer 1A. The gradient magnetic field nulling coil 8 generates a magnetic field according to the current supplied from the coil power supply 6 to cancel the gradient magnetic field. The gradient magnetic field nulling coil 8 has, for example, a pair of gradient magnetic field nulling coils 8A and 8B. The pair of gradient magnetic field nulling coils 8A and 8B are arranged with the optically pumped magnetometer 1A interposed therebetween (for example, on the left and right of the subject). The pair of gradient magnetic field nulling coils 8A and 8B generate a magnetic field, which is opposite to the gradient magnetic field at the position of the optically pumped magnetometer 1A and has approximately the same magnitude as the gradient magnetic field, according to the current supplied from the coil power supply 6. The direction of the magnetic field is, for example, the X-axis direction, the Y-axis direction, and the Z-axis direction. The gradient magnetic field at the position of the optically pumped magnetometer 1A is canceled by a magnetic field generated by the gradient magnetic field nulling coil 8, the magnetic field being opposite to the gradient magnetic field and having approximately the same magnitude as the gradient magnetic field. In this manner, the gradient magnetic field nulling coil 8 cancels the gradient magnetic field at the position of the optically pumped magnetometer 1A.

In addition, the gradient magnetic field nulling coil 8 has a role as a gradient magnetic field coil for generating a gradient magnetic field during MR image measurement. The gradient magnetic field nulling coil 8 generates a gradient magnetic field having a selective gradient in the X-axis direction, the Y-axis direction, and the Z-axis direction according to the current supplied from the coil power supply 6.

The active shield coil 9 is a coil for cancelling the fluctuating magnetic field at the position of the optically pumped magnetometer 1A. The active shield coil 9 generates a magnetic field according to the current supplied from the coil power supply 6 to cancel the fluctuating magnetic field. The active shield coil 9 has, for example, a pair of active shield coils 9A and 9B. The pair of active shield coils 9A and 9B are arranged with the optically pumped magnetometer 1A interposed therebetween (for example, on the left and right of the subject). The pair of active shield coils 9A and 9B generate a magnetic field, which is opposite to the fluctuating magnetic field at the position of the optically pumped magnetometer 1A and has approximately the same magnitude as the fluctuating magnetic field, according to the current supplied from the coil power supply 6. The direction of the magnetic field is, for example, the X-axis direction, the Y-axis direction, and the Z-axis direction. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field. In this manner, the active shield coil 9 cancels the fluctuating magnetic field at the position of the optically pumped magnetometer 1A.

The pump laser 10 is a laser device that generates pump light. The pump light emitted from the pump laser 10 is incident on each of the multiple optically pumped magnetometers 1A and the optically pumped magnetometers 23A by fiber branching.

The probe laser 11 is a laser device that generates probe light. The probe light emitted from the probe laser 11 is incident on each of the multiple optically pumped magnetometers 1A and the optically pumped magnetometers 23A by fiber branching.

The amplifier 12A is a device or circuit that amplifies an output result signal from the OPM module 1 (specifically, the read circuit 1C) and outputs the signal to the control device 5.

The amplifier 12B is a device or circuit that amplifies an output result signal from the OPM module 23 (specifically, the read circuit 23C) and outputs the signal to the control device 5.

The heater controller 13 is a temperature adjusting device connected to a heater for heating the cell of the optically pumped magnetometer 1A and the cell of the optically pumped magnetometer 23A and a thermocouple (not shown) for measuring the temperature of each cell. The heater controller 13 adjusts the temperature of each cell by receiving the temperature information of the cell from the thermocouple and adjusting the heating of the heater based on the temperature information.

The electromagnetic shield 14 is a shield member for shielding high-frequency (for example, 10 kHz or higher) electromagnetic noise. For example, the electromagnetic shield 14 is formed of a mesh woven with metal threads, a non-magnetic metal plate such as aluminum, or the like. The electromagnetic shield 14 is arranged so as to surround the OPM modules 1 and 23, the transmission coil 21, the receive coil 22, the output coil 24, the magnetic sensor for geomagnetic field cancellation 2, the magnetic sensor for active shield 3, the non-magnetic frame 4, the geomagnetic field nulling coil 7, the gradient magnetic field nulling coil 8, and the active shield coil 9. The electromagnetic shield 14 can prevent noise in the 300 kHz band, which is a measurement frequency, from entering the receive coil 22 to increase the noise during MR image measurement. In addition, it is possible to prevent high-frequency noise from entering the optically pumped magnetometer 1A to cause an unstable operation during the measurement of the brain's magnetic field.

Subsequently, a characteristic process performed by the control device 5 will be described. The control device 5 generates a brain's magnetic field distribution and an MR image as described above. Then, the control device 5 aligns the generated brain's magnetic field distribution with the MR image. In addition, in the MEG coordinate system (magnetoencephalographic coordinate system), which is the coordinates on the brain's magnetic field distribution, the position of the optically pumped magnetometer 1A and the position of the marker 16 are determined in advance at the time of designing the non-magnetic frame 4. In addition, the MEG coordinate system (magnetoencephalographic coordinate system) is a coordinate system that defines the relative positional relationship between the optically pumped magnetometer 1A and the measured brain's magnetic field distribution.

Figure 2B:
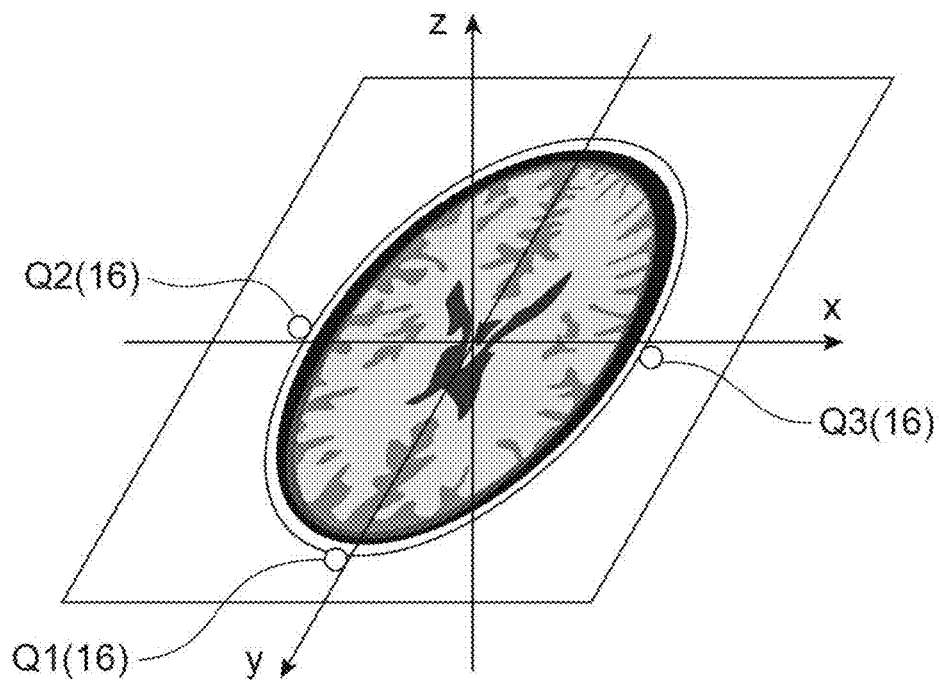
FIG. 2B is a schematic diagram showing an example of an MR image acquired by a control device according to the embodiment.

First, the control device 5 performs an extraction process for extracting the marker 16 from the generated MR image. Then, the control device 5 performs an acquisition process for acquiring the position of the marker 16 extracted by the extraction process in the MRI coordinate system that is a coordinate system on the MR image. FIG. 2B is a diagram showing an MR image. The control device 5 extracts markers Q1, Q2, and Q3, which are markers 16 displayed on the MR image. The control device 5 acquires the position coordinates of the markers Q1, Q2, and Q3 in the MRI coordinate system based on the extraction result.

Subsequently, the control device 5 performs an estimation process for estimating conversion information for converting the MEG coordinate system into the MRI coordinate system based on the position of the marker 16 in the MEG coordinate system and the position of the marker 16 in the MRI coordinate system acquired by the acquisition process.

In the estimation process, first, the control device 5 acquires the position coordinates of the marker 16 in the MEG coordinate system. In the example shown in FIG. 2A, the MEG coordinate system, which is a coordinate system corresponding to the non-magnetic frame 4, is shown. The control device 5 acquires the position coordinates of the markers P1, P2, and P3 in the MEG coordinate system in advance from the design information of the non-magnetic frame 4.

Then, the control device 5 estimates an affine transformation matrix T, which is conversion information for converting the MEG coordinate system into the MRI coordinate system, from the position coordinates of the markers P1, P2, and P3 in the MEG coordinate system and the position coordinates of the markers Q1, Q2, and Q3 in the MRI coordinate system by using the following Equation (1).

$$P_{MRI} = TP_{MEG} \quad (1)$$

In the above Equation (1), $P_{MRI}$ represents a position vector in the MRI coordinate system, $P_{MEG}$ represents a position vector in the MEG coordinate system, and T represents an affine transformation matrix (conversion information). The affine transformation matrix T can be determined if the positional relationship among three points is known between the MRI coordinate system and the MEG coordinate system. In the example shown in FIGS. 2A and 2B, the three points in the MRI coordinate system can be the markers P1, P2, and P3, and the three points in the MEG coordinate system can be the markers Q1, Q2, and Q3. Therefore, the control device 5 can estimate the affine transformation matrix T by using the marker 16.

Figure 4A:
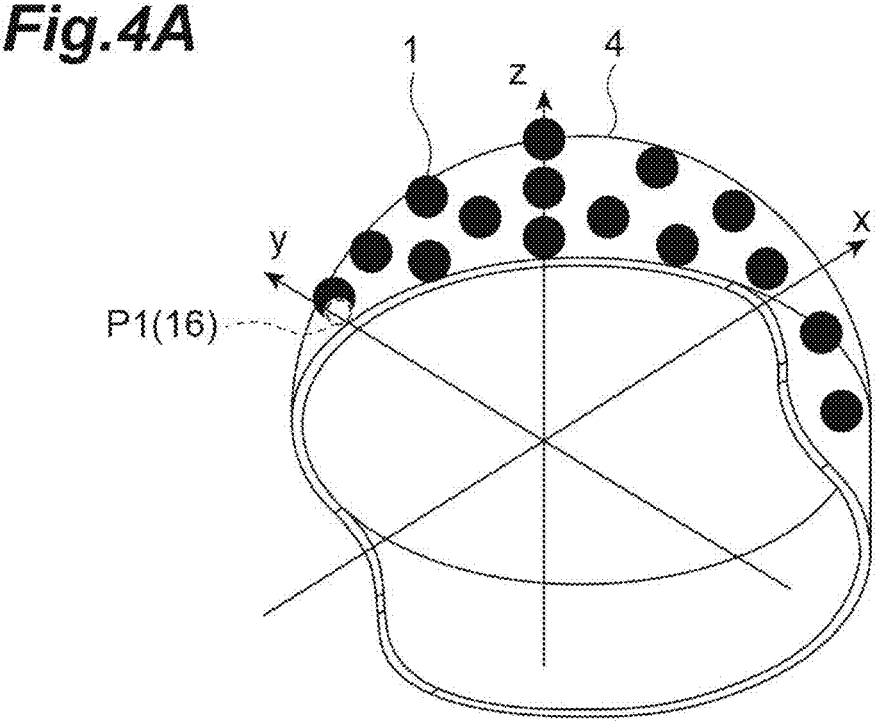
FIG. 4A is a schematic diagram showing an example of a non-magnetic frame according to the embodiment.
Figure 4B:
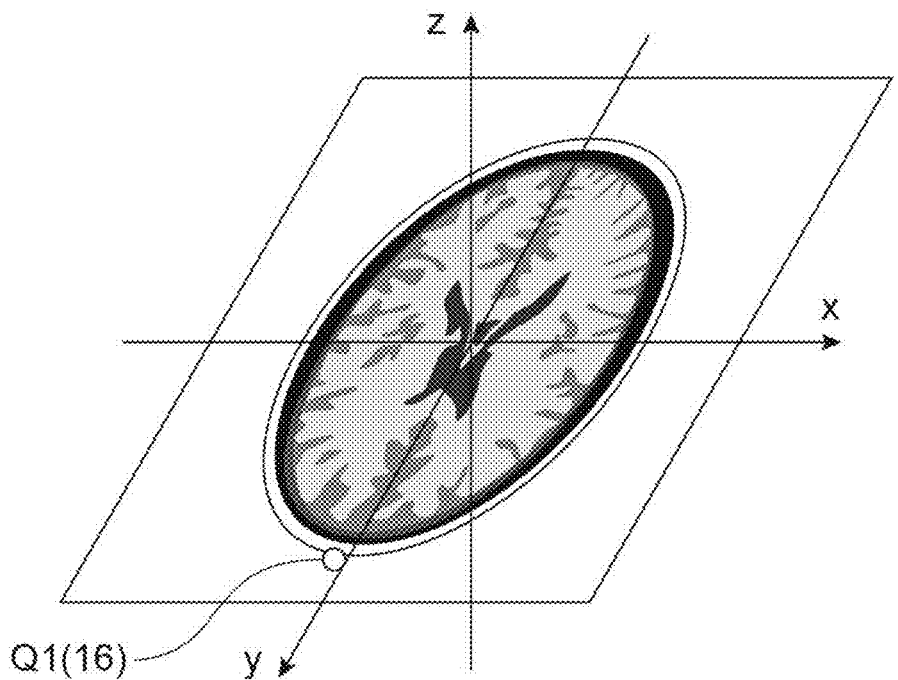
FIG. 4B is a schematic diagram showing an example of an MR image acquired by the control device according to the embodiment.

In addition, the number of markers 16 arranged in the non-magnetic frame 4 may be at least one. The substitutes for the other two markers 16 when the number of the markers 16 is one may be those displayed on the MR image, and are, for example, parts such as the left and right ears of the subject. In the example shown in FIGS. 4A and 4B, the marker P1 arranged at a position corresponding to the glabella of the subject is the marker 16 arranged in the non-magnetic frame 4, and is displayed as the marker Q1 on the MR image. The control device 5 can estimate the affine transformation matrix T by using one marker 16 and two parts such as the left and right ears of the subject.

Figure 5A:
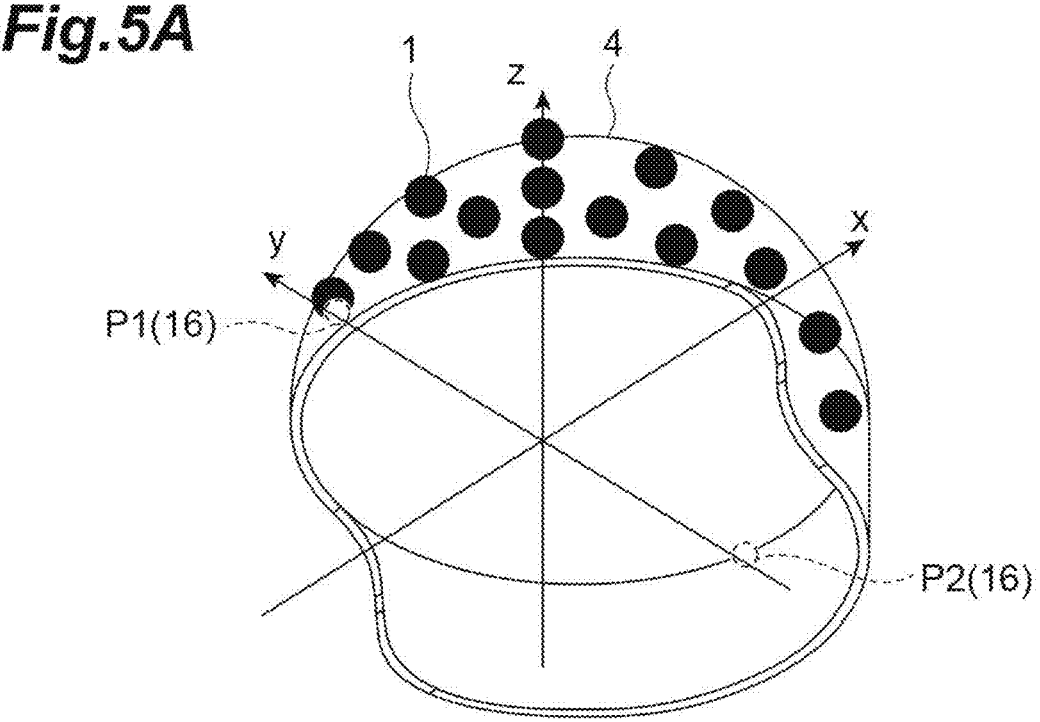
FIG. 5A is a schematic diagram showing an example of a non-magnetic frame according to the embodiment.
Figure 5B:
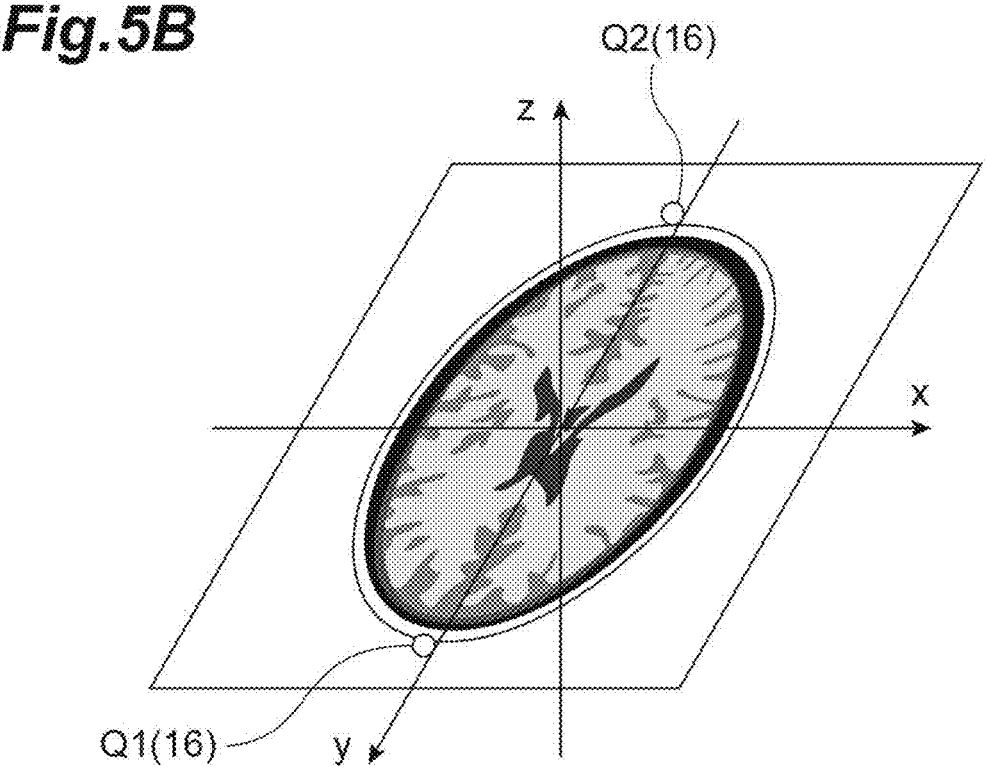
FIG. 5B is a schematic diagram showing an example of an MR image acquired by the control device according to the embodiment.

In addition, in the example shown in FIGS. 5A and 5B, the markers P1 and P2 arranged at positions corresponding to the glabella and the back of the head of the subject are the markers 16 arranged on the non-magnetic frame 4, and are displayed as the markers Q1 and Q2 on the MR image. When the number of markers 16 is two as described above, the control device 5 uses a part, such as the left ear or the right ear of the subject, as a substitute for the other marker 16. The control device 5 can estimate the affine transformation matrix T by using these two markers 16 and one part such as the left or right ear of the subject.

The control device 5 performs an alignment process for performing alignment between the brain's magnetic field distribution and the MR image by projecting the brain's magnetic field distribution onto the MRI coordinate system using the conversion information estimated by the estimation process described above. Specifically, the control device 5 projects the brain's magnetic field distribution in the MEG coordinate system onto the MRI coordinate system by using the affine transformation matrix T, which is information indicating the correspondence between the MEG coordinate system and the MRI coordinate system that has been estimated by the estimation process.

Figure 6:
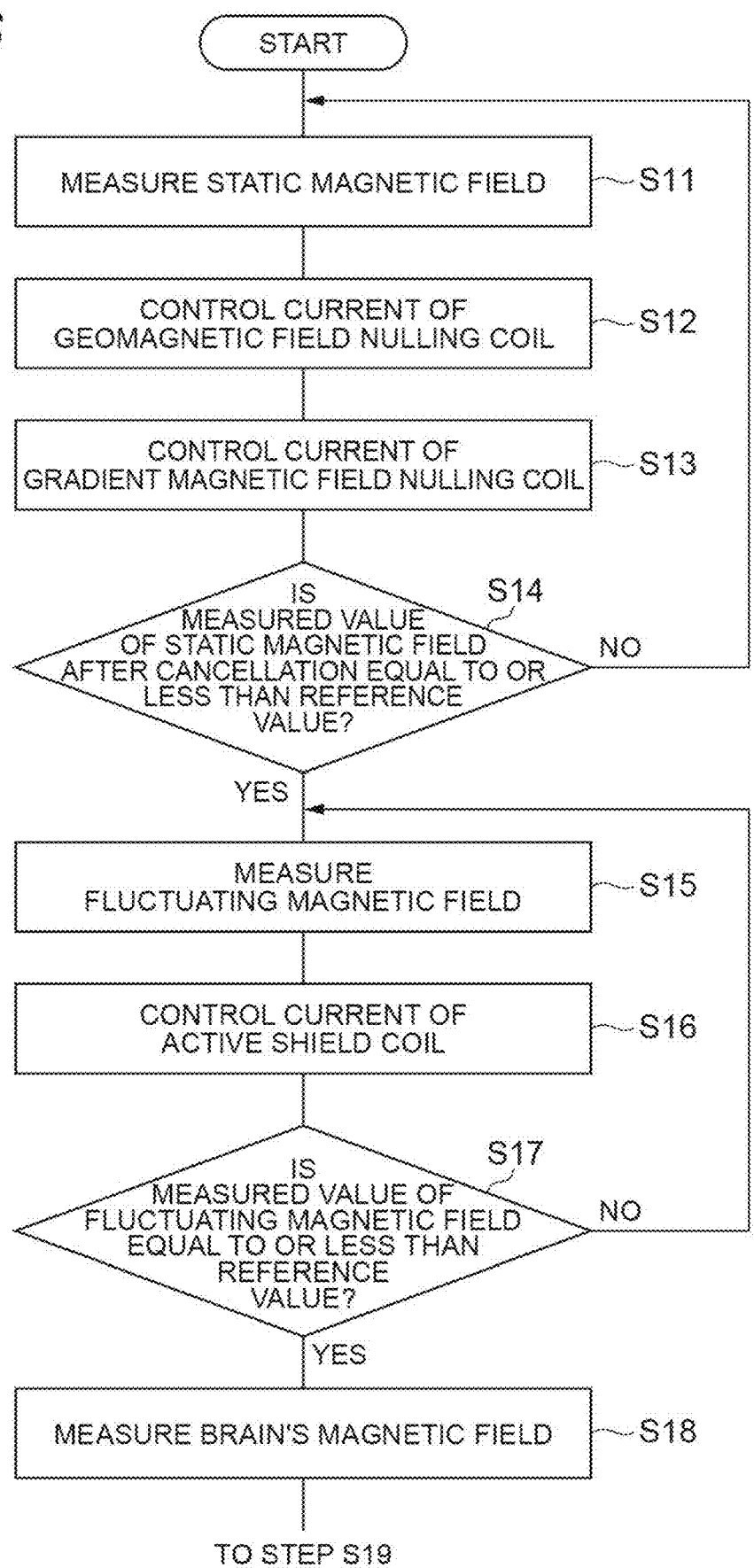
FIG. 6 is a flowchart showing the operation of the brain measurement apparatus according to the embodiment.
Figure 7:
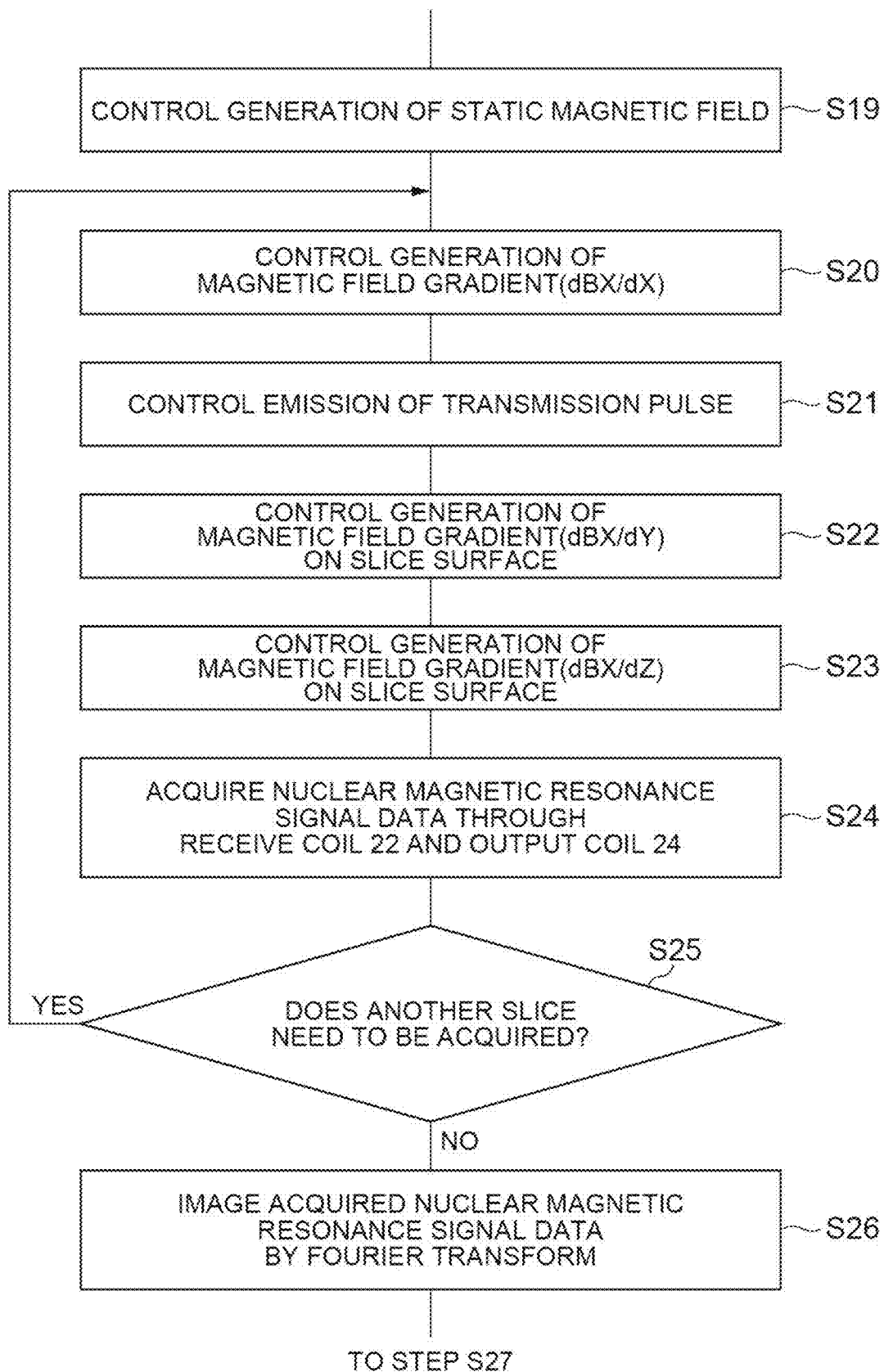
FIG. 7 is a flowchart showing the operation of the brain measurement apparatus according to the embodiment.
Figure 8:
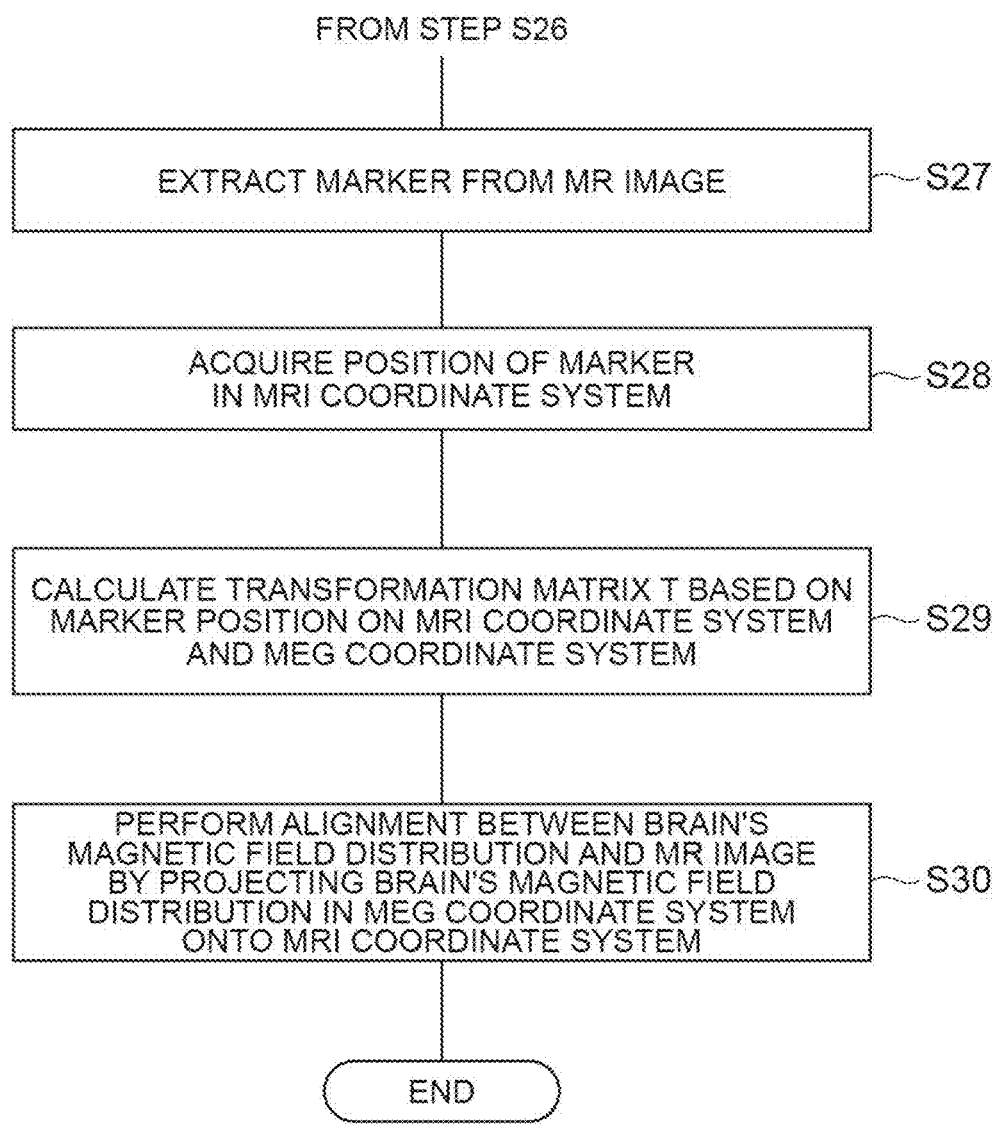
FIG. 8 is a flowchart showing the operation of the brain measurement apparatus according to the embodiment.

Next, a brain measurement method using the brain measurement apparatus M1 according to the embodiment will be described with reference to FIGS. 6 to 8. FIGS. 6 to 8 are flowcharts showing the operation of the brain measurement apparatus M1.

First, when the measurement of the brain's magnetic field starts with the non-magnetic frame 4 attached to the subject, the magnetic sensor for geomagnetic field cancellation 2 measures a magnetic field relevant to the geomagnetic field, which is a static magnetic field (step S11). The magnetic sensor for geomagnetic field cancellation 2 measures the geomagnetic field and the gradient magnetic field at each position of the optically pumped magnetometer 1A, and outputs the measured values to the control device 5.

The control device 5 and the coil power supply 6 control a current for the geomagnetic field nulling coil 7 (step S12). The control device 5 determines a current for the geomagnetic field nulling coil 7 based on the measured value of the magnetic sensor for geomagnetic field cancellation 2 so that a magnetic field opposite to the geomagnetic field at the position of the optically pumped magnetometer 1A and having approximately the same magnitude as the geomagnetic field is generated. More specifically, the control device 5 determines a current for the geomagnetic field nulling coil 7 so that the average value of the measured values of the multiple magnetic sensors for geomagnetic field cancellation 2 approaches zero, for example. The control device 5 outputs a control signal corresponding to the determined current to the coil power supply 6. The coil power supply 6 outputs a predetermined current to the geomagnetic field nulling coil 7 in response to the control signal output from the control device 5. The geomagnetic field nulling coil 7 generates a magnetic field according to the current supplied from the coil power supply 6. The geomagnetic field at the position of the optically pumped magnetometer 1A is canceled by a magnetic field generated by the geomagnetic field nulling coil 7, the magnetic field being opposite to the geomagnetic field and having approximately the same magnitude as the geomagnetic field.

The control device 5 and the coil power supply 6 control a current for the gradient magnetic field nulling coil 8 (step S13). The control device 5 determines a current for the gradient magnetic field nulling coil 8 based on the measured value of the magnetic sensor for geomagnetic field cancellation 2 so that a magnetic field opposite to the gradient magnetic field at the position of the optically pumped magnetometer 1A and having approximately the same magnitude as the gradient magnetic field is generated. More specifically, the control device 5 determines a current for the gradient magnetic field nulling coil 8 so that the deviation from the average value of the measured values of the multiple magnetic sensors for geomagnetic field cancellation 2 is minimized, for example. The control device 5 outputs a control signal corresponding to the determined current to the coil power supply 6. The coil power supply 6 outputs a predetermined current to the gradient magnetic field nulling coil 8 in response to the control signal output from the control device 5. The gradient magnetic field nulling coil 8 generates a magnetic field according to the current supplied from the coil power supply 6. The gradient magnetic field at the position of the optically pumped magnetometer 1A is canceled by a magnetic field generated by the gradient magnetic field nulling coil 8, the magnetic field being opposite to the gradient magnetic field and having approximately the same magnitude as the gradient magnetic field.

The control device 5 determines whether or not the measured value of the static magnetic field (magnetic field relevant to the geomagnetic field) after the cancellation is equal to or less than the reference value (step S14). The measured value of the static magnetic field after the cancellation is a value measured by the magnetic sensors for geomagnetic field cancellation 2 after the static magnetic field is canceled by the geomagnetic field nulling coil 7 and the gradient magnetic field nulling coil 8. The reference value is the magnitude of the magnetic field in which the optically pumped magnetometer 1A normally operates, and can be set to, for example, 1 nT. If the measured value of the static magnetic field is not equal to or less than the reference value ("NO" in step S14), the process returns to step S11. If the measured value of the static magnetic field is equal to or less than the reference value ("YES" in step S14), the process proceeds to step S15.

The magnetic sensor for active shield 3 measures a fluctuating magnetic field (step S15). The magnetic sensor for active shield 3 measures a fluctuating magnetic field at each position of the optically pumped magnetometer 1A and outputs the measured value to the control device 5.

The control device 5 and the coil power supply 6 control a current for the active shield coil 9 (step S16). The control device 5 determines a current for the active shield coil 9 based on the measured value of the magnetic sensor for active shield 3 so that a magnetic field opposite to the fluctuating magnetic field at the position of the optically pumped magnetometer 1A and having approximately the same magnitude as the fluctuating magnetic field is generated. More specifically, the control device 5 determines a current for the active shield coil 9 so that the average value of the measured values of the multiple magnetic sensors for active shield 3 approaches zero, for example. The control device 5 outputs a control signal corresponding to the determined current to the coil power supply 6. The coil power supply 6 outputs a predetermined current to the active shield coil 9 in response to the control signal output from the control device 5. The active shield coil 9 generates a magnetic field according to the current supplied from the coil power supply 6. The fluctuating magnetic field at the position of the optically pumped magnetometer 1A is canceled by a magnetic field generated by the active shield coil 9, the magnetic field being opposite to the fluctuating magnetic field and having approximately the same magnitude as the fluctuating magnetic field.

The control device 5 determines whether or not the measured value of the fluctuating magnetic field after the cancellation is equal to or less than the reference value (step S17). The measured value of the fluctuating magnetic field after the cancellation is a value measured by the magnetic sensor for active shield 3 after the fluctuating magnetic field is canceled by the active shield coil 9. The reference value is a noise level at which the brain's magnetic field can be measured, and can be set to, for example, 1 pT. If the measured value of the fluctuating magnetic field is not less than or equal to the reference value ("NO" in step S17), the process returns to step S15. If the measured value of the fluctuating magnetic field is equal to or less than the reference value ("YES" in step S17), the process proceeds to step S18.

The optically pumped magnetometer 1A measures a brain's magnetic field (step S18). The control device 5 outputs the measurement result acquired by the optically pumped magnetometer 1A to a predetermined output destination. The predetermined output destination may be a memory of the control device 5, a storage device of the control device 5 such as a hard disk, an output device of the control device 5 such as a display, or an external device such as a terminal device connected through a communication interface. Since the static magnetic field (magnetic field relevant to the geomagnetic field) and the fluctuating magnetic field at the position of the optically pumped magnetometer 1A are canceled so as to be equal to or less than a predetermined reference value, the optically pumped magnetometer 1A can measure the brain's magnetic field in a state in which the influence of the static magnetic field (magnetic field relevant to the geomagnetic field) and the influence of the fluctuating magnetic field are avoided. The control device 5 generates the brain's magnetic field distribution of the subject based on the brain's magnetic field acquired by the optically pumped magnetometer 1A. The control device 5 can acquire information regarding the position of the marker 16 in the brain's magnetic field distribution (in the MEG coordinate system) based on the positional relationship between the optically pumped magnetometer 1A and the marker 16 in the non-magnetic frame 4.

Moving to FIG. 7, when MR image measurement starts subsequently with the non-magnetic frame 4 attached to the subject, the control device 5 controls the generation of a static magnetic field in the X-axis direction in the head of the subject by determining a current to be supplied to the geomagnetic field nulling coil 7 for applying the static magnetic field and outputting a control signal to the coil power supply 6 (step S19). Then, the control device 5 controls the generation of an X-axis direction magnetic field gradient ($dB_x/dX$) by determining a current to be supplied to the gradient magnetic field nulling coil 8 for generating the gradient magnetic field and outputting a control signal to the coil power supply 6 (step S20). At the same time, the control device 5 outputs a control signal, which is for controlling the electric power to be supplied to the transmission coil 21, to the transmission coil controller 15 to control the transmission pulse to be emitted to the head of the subject (step S21). As a result, protons on a predetermined slice surface are excited.

In addition, the control device 5 controls the generation of a Y-axis direction magnetic field gradient ($dB_x/dY$) on the slice surface by determining a current to be supplied to the gradient magnetic field nulling coil 8 for generating the gradient magnetic field and outputting a control signal to the coil power supply 6 (step S22). As a result, phase encoding is performed. Then, the control device 5 controls the generation of a Z-axis direction magnetic field gradient ($dB_x/dZ$) on the slice surface by determining a current to be supplied to the gradient magnetic field nulling coil 8 for generating the gradient magnetic field and outputting a control signal to the coil power supply 6 (step S23). As a result, frequency encoding is performed.

At the same time, a nuclear magnetic resonance signal from the proton is output from the OPM module 23 through the receive coil 22 and the output coil 24, and the control device 5 acquires the data of the nuclear magnetic resonance signal (step S24). Thereafter, the control device 5 determines whether or not to acquire nuclear magnetic resonance signal data regarding another slice surface (step S25). As a result of the determination, when nuclear magnetic resonance signal data regarding another slice surface is acquired ("YES" in step S25), the process returns to step S20. On the other hand, when nuclear magnetic resonance signal data regarding another slice surface is not acquired ("NO" in step S25), an MR image is acquired by Fourier-transforming the nuclear magnetic resonance signal data acquired so far (step S26). That is, the control device 5 generates an MR image based on the nuclear magnetic resonance signal. The control device 5 outputs the acquired MR image to a predetermined output destination. The predetermined output destination may be a memory of the control device 5, a storage device of the control device 5 such as a hard disk, an output device of the control device 5 such as a display, or an external device such as a terminal device connected through a communication interface.

Moving to FIG. 8, the control device 5 extracts the marker 16 from the MR image (step S27). Subsequently, the control device 5 acquires the position of the extracted marker 16 in the MRI coordinate system (step S28). In addition, the control device 5 estimates conversion information for converting the MEG coordinate system into the MRI coordinate system based on the position of the marker 16 in the MEG coordinate system and the acquired position of the marker 16 in the MRI coordinate system (step S29). Thereafter, the control device 5 projects the brain's magnetic field distribution onto the MRI coordinate system by using the estimated conversion information to align the brain's magnetic field distribution with the MR image (step S30).

As described above, the brain measurement method according to the embodiment includes: a first step in which, in a state in which the helmet-type non-magnetic frame 4 provided with the optically pumped magnetometer 1A and the marker 16 is attached to the subject's head, the nuclear magnetic resonance signal generated in the subject is detected to generate the MR image, in which the marker 16 is displayed, based on the nuclear magnetic resonance signal (steps S19 to S26) and the brain's magnetic field of the subject is detected by the optically pumped magnetometer 1A to generate the brain's magnetic field distribution based on the brain's magnetic field (steps S11 to S18); and a second step in which the MR image and the brain's magnetic field distribution generated in the first step are aligned with each other (steps S27 to S30). In addition, the second step includes: an extraction step for extracting the marker 16 from the MR image (step S27); an acquisition step for acquiring the position of the marker 16 extracted in the extraction step in the MRI coordinate system that is a coordinate system on the MR image (step S28); an estimation step for estimating conversion information for converting the MEG coordinate system, which is a coordinate system on the brain's magnetic field distribution, into the MRI coordinate system based on the position of the marker 16 in the MEG coordinate system and the position of the marker 16 in the MRI coordinate system acquired in the acquisition step (step S29); and an alignment step for performing alignment between the brain's magnetic field distribution and the MR image by projecting the brain's magnetic field distribution onto the MRI coordinate system using the conversion information estimated in the estimation step (step S30). The specific method for estimating the conversion information is as described above.

[Operational Effects]

Next, the operational effects of the brain measurement apparatus according to the above embodiment will be described.

In the brain measurement apparatus M1 and the brain measurement method according to the present embodiment, since the marker 16 and the optically pumped magnetometer 1A are attached to the non-magnetic frame 4, the positional relationship between the marker 16 and the optically pumped magnetometer 1A is determined by the machining accuracy in the non-magnetic frame 4. This means that the position of the marker 16 can be acquired with high accuracy according to the machining accuracy in the brain's magnetic field distribution generated based on the brain's magnetic field detected by the optically pumped magnetometer 1A. On the other hand, the marker 16 is displayed on the MR image. Therefore, it is possible to acquire information regarding the positional relationship between the brain's magnetic field distribution and the MR image based on the position of the marker 16 in the brain's magnetic field distribution and the position of the marker 16 in the MR image. Therefore, it is possible to align the brain's magnetic field distribution with the MR image more accurately. In addition, since the head position of the subject with respect to the gradient magnetic field coil may change during the measurement of MRI and MEG, it is not easy to align the MR image with the brain's magnetic field distribution. Since the marker 16 is provided on the helmet-type non-magnetic frame 4 to which the optically pumped magnetometer 1A is fixed, the position of the marker 16 is displayed on the MR image. Therefore, it is possible to align the brain's magnetic field distribution with the MR image more accurately. That is, in the brain measurement apparatus M1, it is possible to accurately estimate from which part of the subject's brain the magnetic signal is generated. That is, it is possible to improve the signal source estimation accuracy in the brain measurement apparatus M1.

In the brain measurement apparatus M1 according to the present embodiment, the generator may perform: an extraction process for extracting the marker 16 from the MR image; an acquisition process for acquiring the position of the marker 16 extracted by the extraction process in the MRI coordinate system that is a coordinate system on the MR image; an estimation process for estimating conversion information for converting the MEG coordinate system, which is a coordinate system on the brain's magnetic field distribution, into the MRI coordinate system based on the position of the marker 16 in the MEG coordinate system and the position of the marker 16 in the MRI coordinate system acquired by the acquisition process; and an alignment process for performing alignment between the brain's magnetic field distribution and the MR image by projecting the brain's magnetic field distribution onto the MRI coordinate system using the conversion information estimated by the estimation process. In addition, in the brain measurement method according to the present disclosure, the second step may include: an extraction step for extracting the marker 16 from the MR image; an acquisition step for acquiring the position of the marker 16 extracted in the extraction step in the MRI coordinate system that is a coordinate system on the MR image; an estimation step for estimating conversion information for converting the MEG coordinate system, which is a coordinate system on the brain's magnetic field distribution, into the MRI coordinate system based on the position of the marker 16 in the MEG coordinate system and the position of the marker 16 in the MRI coordinate system acquired in the acquisition step; and an alignment step for performing alignment between the brain's magnetic field distribution and the MR image by projecting the brain's magnetic field distribution onto the MRI coordinate system using the conversion information estimated in the estimation step. In this case, since the conversion information for converting the MEG coordinate system into the MRI coordinate system is estimated from the position of the marker 16 in the MR image and the brain's magnetic field distribution and the brain's magnetic field distribution is projected onto the MRI coordinate system based on the conversion information, it is possible to accurately align the MR image with the brain's magnetic field distribution.

The brain measurement apparatus M1 according to the present embodiment may include the multiple markers 16 attached to different positions of the non-magnetic frame 4. In this case, since the three reference points required for the alignment between the brain's magnetic field distribution and the MR image are acquired more accurately before the measurement, it is possible to align the brain's magnetic field distribution with the MR image more accurately, for example, as compared with a case where there is only one marker 16.

In the brain measurement apparatus M1 according to the present embodiment, the multiple markers 16 may include at least three markers 16 that are not on the same straight line. In this case, since the three reference points required for the alignment between the brain's magnetic field distribution and the MR image are acquired more accurately before the measurement and the three reference points are not on the same straight line, it is possible to align the brain's magnetic field distribution with the MR image more accurately, for example, as compared with a case where there are two markers 16.

In the brain measurement apparatus M1 according to the present embodiment, the marker 16 may include a Beekley marker or a Magnevist solution capsule. In this case, since the marker 16 is displayed more clearly on the MR image, the position of the marker 16 is specified more accurately. Therefore, it is possible to align the brain's magnetic field distribution with the MR image more accurately.

According to the brain measurement apparatus M1 according to the present embodiment, the magnetic field relevant to the geomagnetic field and the fluctuating magnetic field at the position of each of the multiple optically pumped magnetometers 1A for measuring the brain's magnetic field are measured. Then, when measuring the brain's magnetic field, the current flowing through the geomagnetic field nulling coil 7 and the gradient magnetic field nulling coil 8 is controlled based on the multiple measured values of the magnetic field relevant to the geomagnetic field, the current flowing through the active shield coil 9 is controlled based on the multiple measured values of the fluctuating magnetic field, and the magnetic fields are generated in the respective coils 7, 8, and 9. At the positions of the multiple optically pumped magnetometers 1A, the magnetic field relevant to the geomagnetic field is canceled by the magnetic fields generated by the geomagnetic field nulling coil 7 and the gradient magnetic field nulling coil 8, and the fluctuating magnetic field is canceled by the magnetic field generated in the active shield coil 9. As a result, since the magnetic field relevant to the geomagnetic field and the fluctuating magnetic field at the positions of the multiple optically pumped magnetometers 1A are canceled, the multiple optically pumped magnetometers 1A can measure the brain's magnetic field in a state in which the influence of the magnetic field relevant to the geomagnetic field and the influence of the fluctuating magnetic field are avoided.

On the other hand, according to the embodiment described above, when measuring the MR image, the static magnetic field and the gradient magnetic field are applied by controlling the currents flowing through the geomagnetic field nulling coil 7 and the gradient magnetic field nulling coil 8, and the nuclear magnetic resonance signal generated by the transmission of the transmission pulse is detected by the receive coil 22. As a result, the MR image can be measured based on the output of the receive coil 22.

According to such a brain measurement apparatus M1 and a brain measurement method, it is possible to efficiently realize brain's magnetic field measurement and MRI measurement using the same apparatus. In particular, in MRI measurement, since an optically pumped magnetometer is used, a frequency band having a higher sensitivity than the SQUID can be widely adjusted, so that the strength of the applied static magnetic field, that is, the resonance frequency of protons is less limited. A prepolarization coil that has been required since the SQUID operates only at the low resonance frequency, that is, in the low static magnetic field, is not required, and a coolant such as liquid helium required when using the SQUID is also not required. In addition, since the frequency of the signal measured by MRI is also relatively high, a magnetic shield room for reducing magnetic noise during MRI measurement and brain's magnetic field measurement is also not required. As a result, it is possible to reduce the size and cost of the apparatus. In addition, since the time required for prepolarization is approximately the same as the measurement time, the measurement time can also be shortened to ½ in the present embodiment.

In addition, in the present embodiment, since the static magnetic field can be easily turned on and off by turning on and off the current flowing through the geomagnetic field nulling coil 7, it is possible to perform switching between the brain's magnetic field measurement and the MRI measurement in a short time. Therefore, since the brain's magnetic field measurement and the MRI measurement can be sequentially performed on the same subject using the same apparatus, it is possible to reduce registration errors in both measurement results.

As described above, according to the present embodiment, since the MRI measurement can be performed in a low magnetic field, a special room is not required and the T1 contrast can also be increased. In addition, since the active shield coil 9 is used, it is not necessary to measure the brain's magnetic field in the magnetic shield room. Therefore, since the brain's magnetic field measurement and the MRI measurement can be realized by the same apparatus, both measurements can be sequentially performed while the subject is sitting on a chair or the like. In addition, since the cost of the apparatus can be reduced, the above described measurements can also be performed with the subject on a vehicle or the like. As a result, it is possible to contribute to the diagnosis of mental illness, such as depression and schizophrenia, and neurodegenerative diseases, such as dementia.

Here, the brain measurement apparatus M1 uses the geomagnetic field nulling coil 7 for applying a static magnetic field and the gradient magnetic field nulling coil 8 for applying a gradient magnetic field. Therefore, since a coil for geomagnetic field cancellation for brain's magnetic field measurement and a coil for MRI measurement can be shared, it is possible to further reduce the size and cost of the apparatus.

In addition, in the present embodiment, the magnetic field relevant to the geomagnetic field and the fluctuating magnetic field at the positions of the multiple optically pumped magnetometers 1A are canceled at the time of brain's magnetic field measurement, so that the multiple optically pumped magnetometers 1A can measure the brain's magnetic field in a state in which the influence of the magnetic field relevant to the geomagnetic field and the influence of the fluctuating magnetic field are reliably avoided. As a result, the brain's magnetic field can be measured with high accuracy without using the magnetic shield room. Such an operation can be realized even if the head of the subject moves.

In addition, each of the geomagnetic field nulling coil 7, the gradient magnetic field nulling coil 8, and the active shield coil 9 is formed by a pair of coils arranged with multiple optically pumped magnetometers 1A interposed therebetween. According to such a configuration, the magnetic field relevant to the geomagnetic field and the fluctuating magnetic field at the positions of the multiple optically pumped magnetometers 1A interposed between the pair of coils are effectively canceled. In this manner, the magnetic field relevant to the geomagnetic field and the fluctuating magnetic field can be appropriately canceled by a simple configuration.

In addition, the brain measurement apparatus M1 further includes the output coil 24 electrically connected to the receive coil 22 through a cable and another optically pumped magnetometer 23A for detecting the magnetic signal output by the output coil 24. According to such a configuration, it is possible to avoid the influence of the static magnetic field applied at the time of MRI measurement on the detection signal in another optically pumped magnetometer 23A, so that the accuracy of MR image measurement can be improved. That is, for example, the frequency of the nuclear magnetic resonance signal generated by protons when a static magnetic field of 7 mT is applied is about 300 kHz, and it is necessary to apply a bias magnetic field of about 40 µT in order to give sensitivity to this frequency in the optically pumped magnetometer 23A. When the optically pumped magnetometer 23A is arranged near the head of the subject, it is difficult to achieve both such a bias magnetic field and a static magnetic field. In the present embodiment, since the receive coil 22 having no sensitivity to the static magnetic field can be arranged near the head and the optically pumped magnetometer 23A can be arranged away from the head, it is possible to detect the nuclear magnetic resonance signal with high sensitivity.

In addition, the multiple optically pumped magnetometers 1A are axial gradiometers having a measurement region and a reference region in a direction perpendicular to the scalp of the subject and coaxially. According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

In addition, the multiple optically pumped magnetometers 1A, the multiple magnetic sensors for geomagnetic field cancellation 2, the multiple magnetic sensors for active shield 3, and the receive coil 22 are fixed to the helmet-type non-magnetic frame 4 attached to the head of the subject. According to such a configuration, the non-magnetic frame 4 attached to the head and the sensors 2 and 3 and the receive coil 22 fixed to the non-magnetic frame 4 move according to the movement of the head of the subject. Therefore, even when the head of the subject moves, it is possible to appropriately cancel the magnetic field relevant to the geomagnetic field and the fluctuating magnetic field at the positions of the multiple optically pumped magnetometers 1A, measure the brain's magnetic field, and perform MRI measurement. As a result, it is possible to suppress registration errors in both measurements.

In addition, the electromagnetic shield 14 for shielding high-frequency electromagnetic noise may be further provided. According to such a configuration, it is possible to prevent high-frequency electromagnetic noise, which is not a measurement target of the magnetoencephalograph, from entering the multiple optically pumped magnetometers 1A. As a result, the measurement of the brain's magnetic field by the multiple optically pumped magnetometers 1A can be stably performed. At the same time, it is possible to prevent noise in the 300 kHz band, which is the measurement frequency of MRI, from entering the receive coil 22 to increase the noise in the MRI measurement.

In addition, the multiple optically pumped magnetometers 1A are configured to be applied a bias magnetic field so as to be sensitive to frequencies included in the range of 0 to 200 Hz, and another optically pumped magnetometer 23A is configured to be applied a bias magnetic field so as to be sensitive to frequencies included in the range of 20 kHz to 500 kHz. With such a configuration, the measurement sensitivity of the brain's magnetic field can be increased, and at the same time, the accuracy of the MRI measurement can also be improved.

Modification Examples

In the above embodiment, one aspect of the present disclosure has been described. Therefore, the present disclosure is not limited to the above-described brain measurement apparatus and brain measurement method, and can be arbitrarily modified.

As long as the marker 16 can be displayed as a bright spot in the MR image and contain a material having sufficient proton density and appropriate times T1 and T2, the marker 16 is not limited to including the Beekley marker or the Magnevist solution capsule. For example, the marker 16 may contain a liquid.

The shape of the marker 16 is preferable as long as the position of the center of gravity of the marker 16 can be derived in the MR image when the marker 16 is displayed on the MR image. The shape of the marker 16 is not limited to the spherical shape, and may be, for example, a rectangular parallelepiped shape, a cubic shape, or any other shape other than the above.

The position of the marker 16 on the non-magnetic frame 4 is not limited to the position corresponding to the glabella, the back of the head, and the temple of the subject as long as the marker 16 can be displayed on the MR image. For example, the position of the marker 16 on the non-magnetic frame 4 may be a position corresponding to the crown of the subject, or may be a position other than the above. In addition, as long as the substitute for the marker 16 can be displayed on the MR image, the substitute for the marker 16 may be a part other than the subject's ear, or may be a structure of the non-magnetic frame 4 instead of the subject's part.

In addition, when the number of markers 16 is less than 3, the position of the substitute for each marker 16 may be set in advance or may be specified by using a predetermined method.

The conversion information is not limited to the affine transformation matrix T as long as the conversion information is information for converting the MEG coordinate system into the MRI coordinate system. For example, the conversion information may be other kinds of information represented by something other than the matrix.

Although the active shield coil 9 has been described as having a pair of active shield coils 9A and 9B, the active shield coil 9 may be arranged as a three-coil system for each OPM module 1 (optically pumped magnetometer 1A). In this case, the control device 5 determines a current for the active shield coil 9 so that a magnetic field opposite to the components of the fluctuating magnetic field in the three directions (x axis, y axis, and z axis) at the position of the optically pumped magnetometer 1A and having approximately the same magnitude as the components of the fluctuating magnetic field is generated. The control device 5 outputs a control signal corresponding to the determined current relevant to each of the active shield coils 9, which are arranged as a three-coil system, to the coil power supply 6. According to such a configuration, the power consumption for cancelling the fluctuating magnetic field can be made relatively small.

In addition, when measuring the MR image, the control device 5 may set the current flowing through the gradient magnetic field nulling coil 8 so as to cancel the gradient magnetic field relevant to the geomagnetic field, or may set the current flowing through the gradient magnetic field nulling coil 8 so as not to cancel the gradient magnetic field relevant to the geomagnetic field. Since the magnitude of the gradient magnetic field is about several μT and is about two orders of magnitude lower than that of the static magnetic field, high accuracy can be maintained without cancellation when acquiring the MR image.

In addition, the brain measurement apparatus M1 of the embodiment described above may not include the optically pumped magnetometer 23A, or may have a configuration in which the control device 5 directly detects the output from the receive coil 22 through the amplifier.

In addition, the optically pumped magnetometer 1A is not limited to the pump & probe type that uses pump light and probe light, and may be a zero field type optically pumped magnetometer that uses circularly polarized light that also serves as pump light and probe light. In this zero field type, light can be emitted to the cell and a periodic bias magnetic field can be applied to the cell for the lock-in detection of the magnetic field, and the deviation from the zero magnetic field can be measured as the brain's magnetic field.

In addition, in the brain measurement apparatus M1 of the embodiment described above, the position of the non-magnetic frame 4 may be optically measurable. For example, a marker attached to the periphery of the lower end of the non-magnetic frame 4 at intervals of 120° and a camera facing the non-magnetic frame 4 may be provided so that the position variation of the helmet can be measured by using the camera. This measurement result can be used at the time of MRI measurement. For example, the control device 5 can calibrate the MR image by calculating the relative position between the gradient magnetic field nulling coil 8 and the receive coil 22 using the measurement result. As a result, a high-resolution MR image can be acquired even if the head of the subject moves. This is a useful configuration for MRI measurement of a subject whose head is difficult to fix, such as an infant. In addition, at the time of brain's magnetic field measurement, even if the position of the head is displaced, the magnetic field at the position of the optically pumped magnetometer 1A in the displaced state is canceled so as to be zero. Therefore, the need to measure the position of the non-magnetic frame 4 is low, but the position information of the non-magnetic frame 4 may be used to generate a zero magnetic field.

The above embodiment will be noted below.

[Note 1] A Brain Measurement Apparatus, Including:
  a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field;
  an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse; and
  a controller configured to, when measuring the brain's magnetic field, control a current to be supplied to the geomagnetic field nulling coil and a current to be supplied to the active shield coil based on measured values of the multiple magnetic sensors for geomagnetic field cancellation and measured values of the multiple magnetic sensors for active shield and, when measuring an MR image, control the static magnetic field and the gradient magnetic field by controlling currents to be supplied to the static magnetic field coil and the gradient magnetic field coil and generate an MR image based on an output of the receive coil.

[Note 2] the Brain Measurement Apparatus Described in Note 1,
  in which the geomagnetic field nulling coil is formed by a geomagnetic field nulling coil for cancelling a magnetic field of the geomagnetic field and a gradient magnetic field nulling coil for cancelling a gradient magnetic field of the geomagnetic field.

[Note 3] the Brain Measurement Apparatus Described in Note 1 or 2,
  in which the controller determines a current to be supplied to the geomagnetic field nulling coil so as to generate a magnetic field for canceling the magnetic field relevant to the geomagnetic field, and determines a current to be supplied to the active shield coil so as to generate a magnetic field for canceling the fluctuating magnetic field.

[Note 4] the Brain Measurement Apparatus Described in any One of Notes 1 to 3,
  in which each of the geomagnetic field nulling coil and the active shield coil is a pair of coils arranged with the multiple optically pumped magnetometers interposed therebetween.

[Note 5] the Brain Measurement Apparatus Described in any One of Notes 1 to 4, Further Including:
  an output coil that is electrically connected to the receive coil and is configured to output a magnetic signal based on a current flowing through the receive coil; and
  another optically pumped magnetometer configured to detect the magnetic signal output by the output coil, in which the controller generates the MR image based on the magnetic signal detected by the another optically pumped magnetometer.

[Note 6] the Brain Measurement Apparatus Described in any One of Notes 1 to 5,
in which the multiple optically pumped magnetometers are axial gradiometers having a measurement region and a reference region in a direction perpendicular to the scalp of a subject and coaxially.

[Note 7] the Brain Measurement Apparatus Described in any One of Notes 1 to 6,
in which the multiple optically pumped magnetometers, the multiple magnetic sensors for geomagnetic field cancellation, the multiple magnetic sensors for active shield, and the receive coil are fixed to a helmet-type non-magnetic frame attached to the head of a subject.

[Note 8] the Brain Measurement Apparatus Described in any One of Notes 1 to 7, Further Including:
an electromagnetic shield for shielding high-frequency electromagnetic noise.

[Note 9] The brain measurement apparatus described in Note 5,
in which the multiple optically pumped magnetometers are configured to be applied a bias magnetic field so as to be sensitive to frequencies included in a range of 0 to 200 Hz, and
the another optically pumped magnetometer is configured to be applied a bias magnetic field so as to be sensitive to frequencies included in a range of 20 kHz to 500 kHz.

[Note 10] A brain measurement method using a magnetoencephalograph including multiple optically pumped magnetometers configured to measure a brain's magnetic field, multiple magnetic sensors for geomagnetic field cancellation configured to measure a magnetic field relevant to geomagnetic field at a position of each of the multiple optically pumped magnetometers, multiple magnetic sensors for active shield configured to measure a fluctuating magnetic field at the position of each of the multiple optically pumped magnetometers, a geomagnetic field nulling coil for cancelling the magnetic field relevant to the geomagnetic field, and an active shield coil for cancelling the fluctuating magnetic field and an MRI apparatus including a static magnetic field coil for applying a static magnetic field, a gradient magnetic field coil for applying a gradient magnetic field, a transmission coil for transmitting a transmission pulse having a predetermined frequency, and a receive coil for detecting a nuclear magnetic resonance signal generated by the transmission of the transmission pulse, the method including:
when measuring the brain's magnetic field, controlling a current to be supplied to the geomagnetic field nulling coil and a current to be supplied to the active shield coil based on measured values of the multiple magnetic sensors for geomagnetic field cancellation and measured values of the multiple magnetic sensors for active shield; and
when measuring an MR image, controlling the static magnetic field and the gradient magnetic field by controlling currents to be supplied to the static magnetic field coil and the gradient magnetic field coil and generating an MR image based on an output of the receive coil.

[Note 11] the Brain Measurement Method Described in Note 10,
in which the geomagnetic field nulling coil is formed by a geomagnetic field nulling coil for cancelling a magnetic field of the geomagnetic field and a gradient magnetic field nulling coil for cancelling a gradient magnetic field of the geomagnetic field.

What is claimed is:

1. A brain measurement apparatus configured to generate an MR image and a brain's magnetic field distribution of a subject, comprising:
an MRI module having a transmission coil configured to transmit a transmission pulse toward the subject and a detection coil configured to detect a nuclear magnetic resonance signal generated in the subject by the transmission pulse;
an optically pumped magnetometer configured to detect a brain's magnetic field of the subject;
a generator configured to generate the MR image based on the nuclear magnetic resonance signal detected by the detection coil and to generate the brain's magnetic field distribution based on the brain's magnetic field detected by the optically pumped magnetometer;
a fiducial marker configured to be placed on a head of the subject and displayed on the MR image generated by the generator; and
a helmet-type frame to which the detection coil, the optically pumped magnetometer, and the fiducial marker are attached and which is attached to the head of the subject, wherein the detection coil of the MRI module is located closer to a scalp of the head of the subject inside the helmet-type frame than is the optically pumped magnetometer.

2. The brain measurement apparatus according to claim 1, wherein the generator performs: an extraction process extracting the fiducial marker from the MR image;
an acquisition process acquiring a position of the fiducial marker extracted by the extraction process in an MRI coordinate system that is a coordinate system on the MR image;
an estimation process estimating conversion information configured to convert a magnetoencephalographic coordinate system, which is a coordinate system on the brain's magnetic field distribution, into the MRI coordinate system based on a position of the fiducial marker in the magnetoencephalographic coordinate system and the position of the fiducial marker in the MRI coordinate system acquired by the acquisition process; and
an alignment process performing alignment between the brain's magnetic field distribution and the MR image by projecting the brain's magnetic field distribution onto the MRI coordinate system using the conversion information estimated by the estimation process.

3. The brain measurement apparatus according to claim 1, further comprising:
multiple fiducial markers attached to different positions of the frame.

4. The brain measurement apparatus according to claim 3, wherein the multiple fiducial markers include at least three fiducial markers that are not on the same straight line.

5. The brain measurement apparatus according to claim 1, wherein the fiducial marker has a sufficient proton density to be displayed as a bright spot in the MR image.

6. A brain measurement method for generating an MR image and a brain's magnetic field distribution of a subject, comprising:
a first step in which, in a state in which a helmet-type frame provided with an optically pumped magnetometer and a marker is attached to a head of the subject such that a detection coil is located closer to a scalp of the head of the subject inside the helmet-type frame than is the optically pumped magnetometer, a nuclear magnetic resonance signal generated in the subject and the marker is detected to generate the MR image including the marker, based on the nuclear magnetic resonance signal, and a brain's magnetic field of the subject is detected by an optically pumped magnetometer to generate the brain's magnetic field distribution based on the brain's magnetic field; and a second step in which the MR image and the brain's magnetic field distribution generated in the first step are aligned with each other.

7. The brain measurement method according to claim 6, wherein the second step includes:

an extraction step extracting the marker from the MR image;

an acquisition step acquiring a position of the marker extracted in the extraction step in an MRI coordinate system that is a coordinate system on the MR image;

an estimation step estimating conversion information configured to convert a magnetoencephalographic coordinate system, which is a coordinate system on the brain's magnetic field distribution, into the MRI coordinate system based on a position of the marker in the magnetoencephalographic coordinate system and the position of the marker in the MRI coordinate system acquired in the acquisition step; and an alignment step performing alignment between the brain's magnetic field distribution and the MR image by projecting the brain's magnetic field distribution onto the MRI coordinate system using the conversion information estimated in the estimation step.

* * * * *